United States Patent
Phopase et al.

(10) Patent No.: US 10,166,314 B2
(45) Date of Patent: *Jan. 1, 2019

(54) REGENERATIVE PROSTHESES AS ALTERNATIVES TO DONOR CORNEAS FOR TRANSPLANTATION

(71) Applicant: UAB Ferentis, Vilnius (LT)

(72) Inventors: Jaywant Phopase, Linkoping (SE); May Griffith, Linkoping (SE); Mohammad Mirazul Islam, Linkoping (SE); Ramunas Valiokas, Trakai (LT); Ranjithkumar Ravichandran, Linkoping (SE); Vytautas Cepla, Vilnius (LT); Zivile Ruzele, Nemencine (LT); Tomas Rakickas, Vilnius (LT)

(73) Assignee: UAB Ferentis, Vilnius (LV)

( * ) Notice: Subject to any disclaimer, the term of this patent is extended or adjusted under 35 U.S.C. 154(b) by 55 days.

This patent is subject to a terminal disclaimer.

(21) Appl. No.: 15/029,133

(22) PCT Filed: Oct. 14, 2014

(86) PCT No.: PCT/EP2014/072025
§ 371 (c)(1),
(2) Date: Apr. 13, 2016

(87) PCT Pub. No.: WO2015/055656
PCT Pub. Date: Apr. 23, 2015

(65) Prior Publication Data
US 2016/0250383 A1    Sep. 1, 2016

(30) Foreign Application Priority Data

Oct. 14, 2013 (SE) ..................... 1351214

(51) Int. Cl.
*A61L 27/26* (2006.01)
*A61L 27/22* (2006.01)
(Continued)

(52) U.S. Cl.
CPC .............. *A61L 27/26* (2013.01); *A61F 2/142* (2013.01); *A61L 27/227* (2013.01); *A61L 27/24* (2013.01); *A61L 27/34* (2013.01); *A61L 27/48* (2013.01); *A61L 27/52* (2013.01); *C08F 283/04* (2013.01); *C08F 290/065* (2013.01); *C08J 3/246* (2013.01); *C08J 7/18* (2013.01); *C09D 151/08* (2013.01);
(Continued)

(58) Field of Classification Search
CPC .. C08F 290/065; C08F 283/04; C08F 220/20; C08F 2220/286; C08F 220/18; C08F 220/28; C08F 222/1006; C08L 89/06; C08L 33/08; C08L 33/10; C08L 33/12; C08L 33/02; C08L 101/02; C08L 71/02; A61L 27/26; A61L 27/48; A61L 27/34; A61L 2430/16; A61L 27/24; A61L 27/52; A61L 27/227; A61L 24/046; A61L 15/18; A61L 15/46; A61L 2300/102; A61L 2300/106; A61L 2300/404; A61L 2400/12; A61L 27/22; A61L 127/3813; A61L 27/3834; A61L 27/50; A61L 27/54; A61K 6/0017; A61K 6/0023; A61K 6/0038; A61K 2300/00; A61K 33/34; A61K 33/18; A61K 2800/412; A61K 8/0279; A61K 8/20; A61K 8/25; A61K 47/32; A61K 8/19; A61K 9/0014; A61K 9/06; A61K 9/08; A61K 8/8176; A61K 31/555; A61K 33/38; A61K 8/0283; A61K 8/736; A61K 8/8152; A61K 8/85; A61K 8/87; A01N 59/20; A01N 59/12; A01N 25/12; A01N 59/16; A01N 25/26; A01N 25/10; A01N 25/22; A01N 25/04; A01N 37/46; A01N 43/08; A01N 43/40; A61Q 17/005; A61Q 3/02; A61Q 19/10; A61Q 5/02; C09D 5/14; C09D 5/1618; C09D 151/08; C08K 3/16; C09K 8/524; C09K 8/54; C09K 8/605; C09K 8/805; C09K 19/02; C09K 19/06; C09K 19/544; C09K 19/60; A61F 2/142; C07D 307/58; C08G 65/3331; C08G 65/33317; C08G 65/33396; C09J 171/02; C09J 201/06; C12N 11/04; Y02P 20/588; C07K 14/78; C08J 2389/00; C08J 2433/10; C08J 2471/02; C08J 3/246; C08J 7/18
See application file for complete search history.

(56) References Cited

U.S. PATENT DOCUMENTS

2006/0083773 A1    4/2006  Myung et al.
2007/0233240 A1   10/2007  Frank et al.
(Continued)

FOREIGN PATENT DOCUMENTS

EP       2535041 A1    12/2012
WO    WO-2006042272 A2  4/2006

OTHER PUBLICATIONS

International Search Report PCT/ISA/210 for International Application No. PCT/EP2014/072025 dated Nov. 14, 2014.
(Continued)

*Primary Examiner* — Deborah K Ware
(74) *Attorney, Agent, or Firm* — Harness, Dickey & Pierce, P.L.C.

(57) ABSTRACT

The present disclosure relates to a corneal implant comprising a matrix material and a core part wherein the core part is arranged essentially in the middle of the matrix material. The core part is anti fouling in order to stop cell proliferation across said part. The present disclosure further relates to a method of preparing the said product and the use of the same.

18 Claims, 8 Drawing Sheets

(51) Int. Cl.
  *A61L 27/24*   (2006.01)
  *A61L 27/34*   (2006.01)
  *A61L 27/48*   (2006.01)
  *A61L 27/52*   (2006.01)
  *C08F 290/06*  (2006.01)
  *C08J 3/24*    (2006.01)
  *C08J 7/18*    (2006.01)
  *C09D 151/08*  (2006.01)
  *A61F 2/14*    (2006.01)
  *C08F 283/04*  (2006.01)

(52) U.S. Cl.
  CPC ....... *A61L 2430/16* (2013.01); *C08J 2389/00* (2013.01); *C08J 2433/10* (2013.01); *C08J 2471/02* (2013.01)

(56) References Cited

U.S. PATENT DOCUMENTS

2008/0287342 A1  11/2008  Yu et al.
2011/0182968 A1  7/2011   Myung et al.
2013/0116405 A1  5/2013   Yu et al.

OTHER PUBLICATIONS

International Preliminary Report on Patentability PCT/IPEA/409 for International Application No. PCT/EP2014/072025 dated Dec. 22, 2015.

Falconnet, Didier et al. "Surface engineering approaches to micropattern surfaces for cell-based assays." *Biomaterials* 27 (2006): 3044-3063.

Liu, Wenguang et al. "Collagen-phosphorylcholine interpenetrating network hydrogels as corneal substitutes." *Biomaterials* 30 (2009): 1551-1559.

Myung, David et al. "Design and fabrication of an artificial cornea based on a photolithographically patterned hydrogel construct." *Biomed Microdevices* 9 (2007): 911-922.

TCP    MPC collagen    MPC-MMA (UV    MPC-MMA (UV
       (control)       exposed)       exposed)

A)

B)

REGENERATIVE PROSTHESES AS ALTERNATIVES TO DONOR CORNEAS FOR TRANSPLANTATION

CROSS-REFERENCE TO RELATED APPLICATIONS

This is a National Phase of PCT Patent Application No. PCT/EP2014/072025 filed on Oct. 14, 2014, and claims priority to Swedish Application No. 1351214-0, filed Oct. 14, 2013, the contents of each of which are hereby incorporated by reference in their entirety.

FIELD OF THE INVENTION

The invention is for a regenerative prosthesis (RPro), a combination, duo-function regeneration promoting implant-prosthetic device, and the method of fabricating such a combination implant. The goal is to restore vision to corneal blind patients, supplementing and possibly replacing the use of donated corneas.

BACKGROUND

There is a severe worldwide shortage of donated organs for transplantation. Even when they are available, immune rejection is a major problem. The only widespread treatment for corneal blindness is transplantation of donor cornea, which is also in severe shortage. Corneal limbal epithelial stem cell transplantation is common but only useful when one layer is damaged. Donor corneas are still needed for deeper injuries and allogeneic grafts are still problematic and face a high rate of rejection.

Stem cell transplantation is considered the state-of-the-art and has been applied, with limited success, as a last hope treatment for restoring function to vital organs such as the heart or liver. The state-of-the-art relies on the introduction of adult source stem cells to repopulate badly damaged or diseased areas. Rejection even in the simple, immune-privileged cornea of foreign implanted stem cells is high. In the cornea transplantation using allogeneic donor tissue has remained the gold standard for over a century. Plastic-based prostheses (keratoprostheses or KPro) e.g. Boston KPro and OOKP, have been used to restore vision in severe ocular surface damage but only as last resorts, as they have an unnatural appearance, suffer from complex implantation procedures and most importantly, have serious complications including retroprosthetic membrane formation, calcification, infection, glaucoma. Continuous immunosuppression is required.

The inventors have previously successfully implanted biosynthetic implants made from (recombinant human) collagen (RHC) into 10 patients in a clinical study in Sweden. All 10 patients showed regeneration of corneal tissues and nerves, without the need of sustained immunosuppression over 4 years. We have since then strengthened the implants by introducing a second network of materials by formation of interpenetrating networks (IPNs) of recombinant human collagen and MPC-co-PEGDA (MPC=2-methacryloyloxyethyl phosphorylcholine, PEGDA=polyethylene glycol-diacrylate) (RHC-MPC). This new generation of implants have shown to be safe, and successfully promoted regeneration of corneal cells and nerves in mini-pig and rabbit models, and in two human patients. Still there is a need for an implant that remains optically clear when implanted and where the mechanical properties can be tailored in order to match the surrounding tissue and to enable suturing.

SUMMARY OF THE INVENTION

The present invention relates to a product which functions as a duo-functional regenerative prosthesis (RPro), or an implant, which controls the cell and tissue ingrowth on or into the implant, and the invention further relates to a method for preparing said product and the use of said product.

In a first aspect the present invention relates to a product having a first and a second side and wherein the material comprises a matrix material and a core material wherein the core material is arranged within the matrix material in a limited area of the matrix material and wherein the core material is at least partly exposed at the first and the second side;

wherein the matrix material is a hydrogel comprising a cross-linked extracellular matrix polymers, polypeptides or polysaccharides such as collagen, collagen mimetic peptides, hyaluronic acid or chitosan or mixtures thereof; and wherein the core material is based on olefinic or UV polymerizable monomers or polypeptides or mixtures thereof.

In a second aspect the present invention relates to a method of making the product according to the present invention wherein the method comprises:
providing a matrix polymer and a cross-linker in a suitable solvent;
cross-linking the matrix polymer to form the matrix material;
providing core olefinic monomers or UV polymerizable monomers or polypeptides or a mixtures thereof, and an initiator, optionally in a suitable solvent;
adding the core olefinic monomers or UV polymerizable monomers or polypeptides or a mixtures thereof, and the initiator to the surface or the bulk of the matrix material; and
letting the core olefinic monomers polymerize for a suitable period of time.

In a third aspect the present invention relates to a hydrogel of a cross-linked polymer network comprising
at least one first polymer and at least one second polymer wherein the first polymer is a natural polymer provided with methacrylate and/or acrylate functional groups and the second polymer comprises a synthetic and/or a natural polymer having at least two functional groups selected from thiol, acrylate and/or methacrylate;
wherein the first and the second polymers are cross-linked via said functional groups; and
wherein the total concentration of polymers in the hydrogel is at least 2 weight %.

In a fourth aspect the present invention relates to a method of preparing the hydrogel comprising:
providing a solution of a first polymer comprising a natural polymer comprising methacrylate and/or acrylate functional groups;
providing a second polymer comprising a synthetic and/or a natural polymer having at least two functional groups selected from thiol, acrylate and/or methacrylate, or synthetic and/or natural monomers having thiol. acrylate and/or methacrylate functional groups;
mixing the first and the second polymer, or monomers, in water to a total polymer concentration of at least 2 weight %; and letting the functional groups of the first and the second polymer chains cross-link, optionally applying UV radiation to the mixture when the second polymer has acrylate and/or methacrylate functional groups.

In a fifth aspect the present invention relates to an implant comprising the product according to the present invention.

In a sixth aspect the present invention relates to the use of the product according to the present invention as a barrier device, a coating material, as an anti-wrinkle material or as a model material.

In a seventh aspect the present invention relates to a method of treating a patient with a damaged or malfunctioning cornea comprising replacing the damaged or malfunctioning cornea with the implant according to the present invention.

In an eighth aspect the present invention relates to an injectable composition comprising a first and a second solution wherein the first solution is an aqueous solution comprising a natural polymer comprising methacrylate and/or acrylate functional groups; and the second solution is an aqueous solution comprising a synthetic and/or a natural polymer having two or more functional groups selected from thiol, acrylate and/or methacrylate functional groups; and wherein the polymer concentration in each solution is at least 5 weight %.

In a ninth aspect the present invention relates to a hydrogel comprising collagen mimetic peptides and cross-linking agents.

DETAILED DESCRIPTION OF THE INVENTION

Figure 1:
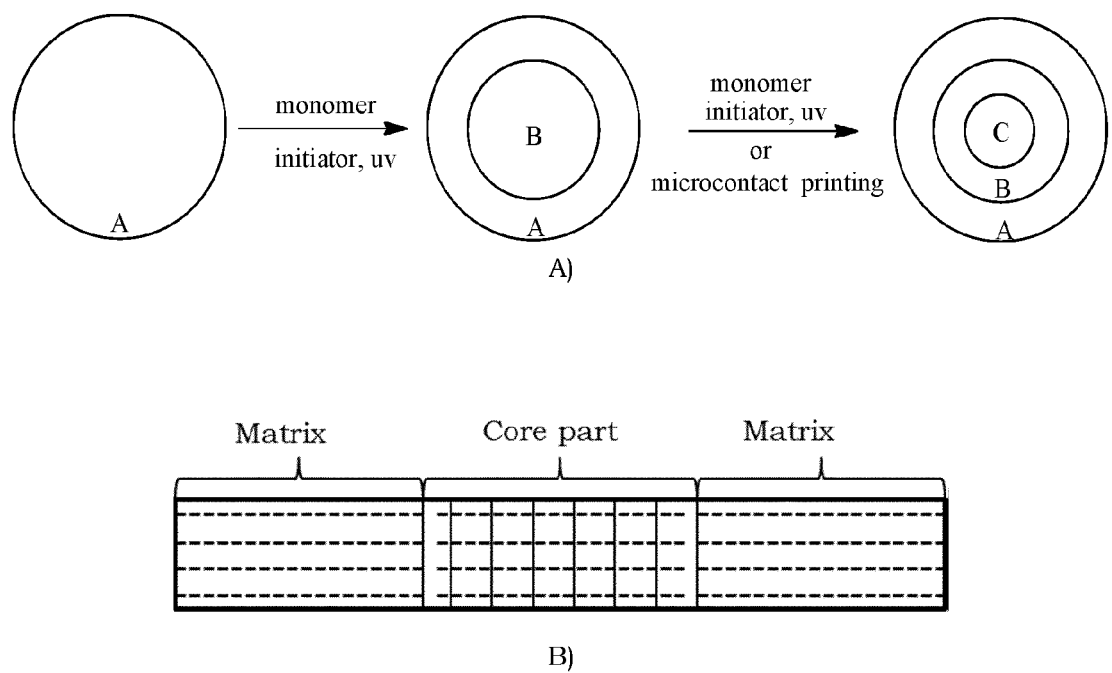
FIG. 1. A) A schematic view of the product. A=Matrix material: Natural/synthetic bio-interactive hydrogel, B=central polymer core with anti-cell/vessel in-growth/antifouling properties, homogeneously embedded into hydrogel A, C=natural/synthetic polymer layer/pattern adhered or covalently bound on the surface of B. B) A schematic cross sectional view of the implant according to the present invention with a matrix and a core part wherein the core part comprises a core material comprising polymerizable monomers or a mixture thereof and the hydrogel of the matrix material.

In the present invention the term "hydrogel" means a gel of hydrophilic natural or synthetic polymers where the dispersion media is water.

In the present invention the term "arm" means side chain connected to a main or common polymeric back bone. For example a two arm polymer has two chains connected at one common point or are connected to one common polymeric back bone. A star polymer or a star co-polymer is a polymer where several polymeric chains are connected at one common point.

In the present application the term "transparent" means a light transmission of at least 80% of light in a wavelength range of 400-700 nm measured by using any suitably technique for example a UV spectrophotometer, and using pure PBS for background reading.

The object of the present invention is to 1) prepare a matrix material (A) which is resistant to enzymatic degradation and supports the cellular ingrowth promoting regeneration, 2) prepare a core material with desired dimensions (diameter of 2-8 mm, preferably 3-5 mm) optionally modified, preferably homogeneously, using synthetic polymer blocking vessel ingrowth, and optionally 3) to surface modify either the whole product or the core material with polymer/bioactive moieties for desired cellular response.

The cornea comprises a largely collagenous extracellular matrix (ECM) interspersed with stromal cells, and sandwiched by epithelial and endothelial cell layers. Natural ECM polymers like collagen are generally mechanically weak, unstable and difficult to process, while some synthetic polymers are strong with controlled stability and easily moldable. On the other hand, hydrogels comprising two or more components (natural and/or synthetic polymers) are generally reliable materials for biomedical applications, due to the superior properties of the final product compared to the properties of each individual component. By generating composite hydrogels based on interpenetrating networks (IPNs), biointeractive properties of natural ECM may be maintained together with the robustness and higher enzymatic stability of the synthetic polymer.

One of the major issues when using transplantation as a treatment is the potential risk of rejection due to inflammation caused by immune response or infection. The normal cornea is avascular and corneal neovascularization induced by inflammation, disease or sutures often result in opacification and rejection of transplanted cornea. Furthermore, in cases where patients lack viable progenitor or stem cells, and stem cell transplantation is not available or an option, there is a need for an alternative treatment. Therefore, the aim of the present invention is to prepare a product, such as an implant or prosthesis, comprising a transparent central core part comprising anti-fouling polymer/polymers which hinder cell migration and vessel ingrowth. The transparent core part can be superimposed onto the matrix material by adding a second component, core monomers optionally together with an initiator, to the matrix material and polymerize it, preferably by UV exposure. The cross-linking may be performed prior to implantation, during the transplantation, during the insertion of the implant, or after implantation. The core part is designed to hinder cells to migrate over or into the said part (e.g. by excluding blood vessels, in growing stromal cells) in order to remain cell-free to allow unhindered transmission of light for vision. In certain cases, e.g. where corneal stem cells are complete depleted and transplantation is not possible, the core part may be modified in order to block migration of non-corneal cells or abnormal cells over the core material to allow unhindered transmission of light.

The product, or implant, of the present invention comprises a matrix material and a core material, and optionally a coating or an imprint or a pattern on the surface of the matrix and/or core material. The matrix material may be an immune compatible biomaterial that is designed to stimulate cell adherence or regeneration, and maybe also repair of damaged tissue, of the human cornea by engaging the patient's own stem or progenitor cells to affect the regeneration. This matrix material can be used alone, where stem or progenitor cells are available to migrate over or into the implant and affect the repair and regeneration.

FIG. 1 discloses a schematic view from above of the present invention where the implant comprises a matrix material (A), a central polymer core with antifouling properties (B), preferably homogeneously arranged in the matrix material A. A natural and/or synthetic polymer layer or coating (C) may further be adhered to or covalently bound to the surface of B. The matrix material (A) may be a hydrogel. See FIG. 7.

In one embodiment the corneal implant (a two dimensional implant having a thickness) has a first and a second opposed surface. The implant comprises a matrix material and a core material wherein the core material is arranged essentially in a central part of the matrix material and the core material is at least partly exposed at the first and the second surface. The matrix material is a hydrogel comprising cross-linked collage and/or collagen mimetic peptides (CMP).

The core material is based on olefinic or UV polymerizable monomers or a mixture thereof and the core material is transparent (i.e. a light transmission of at least 80% of light in the range of 400-700 nm) and anti fouling in order to transmit light and hinder cell integration into or across the core material.

The Matrix Material or the Hydrogel

The matrix material is biointeractive, bio- and immune compatible, and may be used as a scaffold, especially as an implant, for stimulating in-growth of host cells (stem or progenitor cells) to differentiate and regenerate a healthy tissue. The matrix material may be porous with where the pores have a diameter of 1-50 nm, for example 5-20 nm.

The matrix material comprises matrix polymers which may be cross-linked extracellularmatrix (ECM) macromolecules, natural and/or synthetic polymers and/or co-polymers of said polymers (hybrids) mimicking ECM molecules. A non-limiting list of polymers is collagen, collagen mimetic peptides combinations of synergistic cell-interactive motifs, e.g. from cell adhesion peptides, anti-infective peptides (anti-microbial, anti-viral, anti-fungal or synthetic cationic or cell penetrating peptides with anti-infective properties) or combinations thereof or combinations with synthetic polymers for examples PEG. The matrix material may also be an interpenetrating network of natural and/or synthetic analogs of the ECM of the corneal stroma. In one embodiment the matrix material comprises amine groups. In another embodiment the matrix material comprises collagen, native or recombinant collagen.

Figure 7:
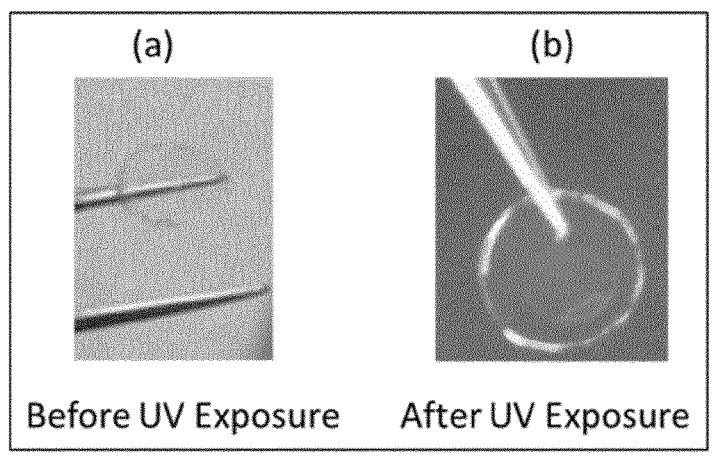
FIG. 7. (a) collagen-MPC hydrogel; (b) collagen-MPC hydrogel with central poly methyl methacrylate core serving as an optic.

The present inventors have prepared hydrogels of collagen or CMP wherein the fibrils of the collagen or CMP are essentially uniaxial orientated or aligned, FIG. 7. The uniaxial orientation is believed to be a result of the higher order of assembly of the fibres which may be a result of the high collagen concentration. Surface modification may also influence the orientation of the fibrils, furthermore without being bound be theory but high pressure freezing of the hydrogel may also influence the orientation of the fibrils, FIG. 7. An essentially uniaxial orientation of the fibrils is believed to increase the mechanical properties of the hydrogel, the transparency and may even influence the cell proliferation and growth.

The generation of a 3D ECM (Extra Cellular Matrix) like environment by cell integration into and across the matrix material the fibers (or fibrils) of the matrix material should be substantially smaller than the cells which have a diameter of around 5-20 micrometers. Synthetic fibres usually have microfibers in the range of 10-50 μm. Thus, cells attached to synthetic microfibers are still in a two dimensional environment with a curvature dependent on the diameter of the microfibers. In addition, because of their micro-scale sizes, the mechanical strength of these polymeric fibers often prevents material structural adaptations from the forces exerted by cells during their adhesion, migration and maturation processes. Therefore the fibres (or fibrils) according to the present invention may have a diameter in the range of 1-30 nm, for example 5-20 nm. The diameter of the fibrils is believed to influence the transparency and makes it possible to make hydrogels with a thickness of up to 1 mm and still be transparent.

The cross-linker for the matrix polymer may be an epoxide or a di-epoxide such as C1-C10 di-epoxide such as 1,3-butadiene di-epoxide, 1,5-hexadiene di-epoxide, or C6-C16 ether di-epoxides such as dimethylallyl ether di-epoxide and 1,4-butanediol diglycidyl ether (BDDGE). By using a di-epoxide, especially BDDGE, the cross-linking step becomes more biocompatible instead of using the less preferred EDC cross-linker. In comparison with EDC cross-linking the epoxide cross-linker also results in improved enzymatic stability (FIG. 6) and better mechanical properties, for example higher elongation at break (Table 1).

Figure 2:
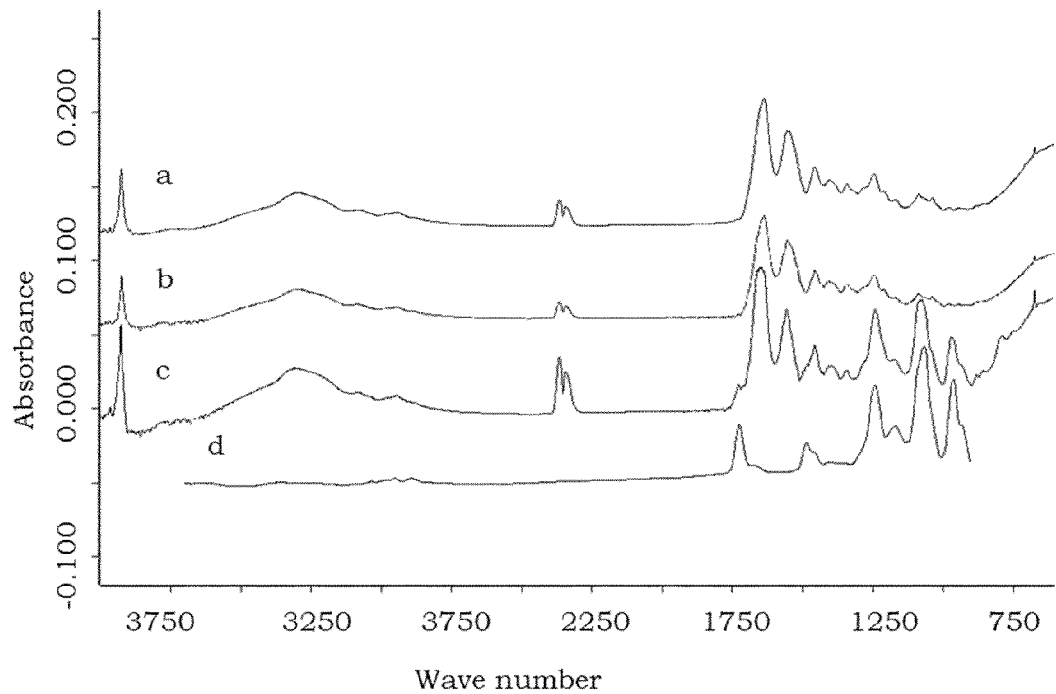
FIG. 2. FTIR spectra showing: a) collagen-EDC/NHS only; b) collagen-MPC formulation without any MPC peaks, c) LiU collagen-MPC showing MPC peaks. The main MPC identification peak is the ester carbonyl peak at 1722 cm−1 together with the peaks at 1065 and 961 cm−1, from the phosphate group; d) MPC only.

The matrix material according to the present invention may be an IPN of one type of ECM molecule and another type of ECM molecule, or of an ECM molecule and a synthetic polymer. In one embodiment the matrix material comprises MPC-co-PEGDA, FIG. 2. In one embodiment the matrix material is an IPN, or a mixture, of MPC-co-PEGDA and collagen (MPC-Coll). A problem has been to prepare such IPNs or mixtures with a high MPC content, however, the present inventors have prepared products with much higher MPC contents than previously disclosed. The higher amount of MPC makes the matrix material and the final product more stable and less susceptible to enzymatic degradation. A higher MPC content also increases the elongation at break but makes the material rigid enough to be sutured.

The matrix material or the hydrogel may be a hydrogel comprising a first polymer which is a natural polymer, for example collagen or collagen mimetic peptides (CMP), and a second polymer comprising a synthetic and/or natural polymer wherein the second polymer preferably is hydrophilic. The second polymer may be partly or fully water soluble which is believed to improve the properties of the obtained hydrogel. The first polymer comprises methacrylate and/or acrylate functional groups while the second polymer comprises thiol, methacrylate and/or acrylate functional groups. In one embodiment the hydrogel is cross-linked or further cross-linked using cross-linking agents for example or EDC and NHS.

The cross-linking agents may be selected from but not limited to EDC, EDC methiodide (1-[3-(Dimethylamino) propyl]-3-ethylcarbodiimide methiodide), DCC (N,N'-Dicyclohexylcarbodiimide), BDDC (1,3-Bis(2,2-dimethyl-1,3-dioxolan-4-ylmethyl)carbodiimide), DIC (N,N'-diisopropylcarbodiimide, $(CH3)_2CH—N═C═N—CH(CH3)_2$), PyOxim[Ethyl cyano(hydroxyimino)acetato-O2] tri-1-pyrrolidinylphosphonium hexafluorophosphate, N-hydroxysuccinimide (HOSu), N-hydroxy-5-norbornene-2,3-dicarboximide (HONB), 1-hydroxybenzotriazole (HOBt), 6-chloro-1-hydroxybenzotriazole (6-Cl-HOBt), 1-hydroxy-7-azabenzotriazole (HOAt), 3-hydroxy-4-oxo-3,4-dihydro-1,2,3-benzotriazine (HODhbt) and its aza derivative (HODhat) or combinations thereof.

When the hydrogel comprises collagen and/or collagen mimetic peptides (CMP) and cross-linking agents, said agents may be EDC and NHS. The molar equivalent ratio of EDC to amine of CMP may be 1:0.5 to 1:3, such as 1:1 to 1:2. The molar ratio of EDC:NHS may be from 2:1 to 1:2, such as 1.5:1 to 1:1.5, or 1:1. By cross-linking the hydrogel via the functional groups (for example methacrylate and thiol) and by the use of EDC:NHS the mechanical properties may be altered and the gelation time may also be shortened.

The first polymer may be selected from collagen, fibrin, cell-interactive proteins (e.g. laminin, fibronectin), hyaluronic acid, chitosan, collagen mimetic peptides, proteins, recombinant proteins or peptides, lignin or cellulose or combinations thereof.

The hydrogel according to the present invention comprises a first and a second polymer. In one embodiment the first polymer is collagen and/or collagen mimetic peptide (CMP). In another embodiment the first polymer is collagen, for example collagen I, collagen II, collagen III, collagen IV or collagen V, or mixtures thereof.

The second polymer may comprise one or more of PEG, PVA, polyethylene glycol-diacrylate (PEGDA), PEG methacrylate (PEGMA), poly(hydroxyethyl methacrylate) (pHEMA), polyethylene glycol methyl ether methacrylate (PEGMEM), poly(pentaerythritol triacrylate), PNIPAAm, silk, collagen, hyaluronic acid, chitosan, collagen mimetic peptides, chimeric peptides based on collagen and cell-interactive peptides, plant lignin, cellulose or plant gum proteins, recombinant proteins or peptides, and co-polymers thereof.

In one embodiment the second polymer is a synthetic polymer, preferably selected from one or more of polyethylene glycol (PEG), polyvinyl alcohol (PVA), polyethylene glycol-diacrylate (PEGDA), PEG methacrylate (PEGMA), poly(hydroxyethyl methacrylate) (pHEMA), polyethylene glycol methyl ether methacrylate (PEGMEM), poly(pentaerythritol triacrylate) or poly(N-isopropylacryl amide) (PNIPAAm). In one embodiment the second polymer is PEG with thiol functional groups. The cell-interactive peptides may be laminin, fibronectin, entactin or vitronectin. In one embodiment the second polymer comprises at least two arms, preferably three or more arms, or four or more arms.

In one embodiment the hydrogel comprises one additional second polymer selected from polyethylene glycol (PEG), polyvinyl alcohol (PVA), polyethylene glycol-diacrylate (PEGDA), PEG methacrylate (PEGMA), poly(hydroxyethyl methacrylate) (pHEMA), polyethylene glycol methyl ether methacrylate (PEGMEM), poly(pentaerythritol triacrylate) or poly(N-isopropylacryl amide) (PNIPAAm). The molar ratio between the second polymer and the additional second polymer may be 3:1 to 0.5:1, such as 2:1 to 1:1.

In one embodiment the second polymer is PEG with 2, 4 or 6 arms. In another embodiment the second polymer or the additional second polymer is PEG with four arms each having thiol groups.

The mechanical properties of the hydrogels can be tuned by varying the methacrylated/acrylated collagen or CMP concentration and/or the methacrylated/acrylated collagen/CMP:thiol molar ratio (or acrylate or methacrylate ratio), thus controlling the degree of crosslinking. Soft hydrogels will be produced with initial collagen/CMP concentrations of 3 and 5 wt %. The collagen/CMP:thiol molar ratio (or acrylate or methacrylate ratio) may be varied from 1 to 10, such as 2 to 8, or 3 to 6. The molar ratio between the functional groups of the first polymer and the functional groups of the second polymer may be from 1:5 to 1:0.5 such as 1:3 to 1:1, or 1:2. Cell viability and proliferation will be assessed on the resulting hydrogels in order to understand the optimal hydrogel mechanical properties that favour cell survival and ultimately regeneration.

Figure 3:
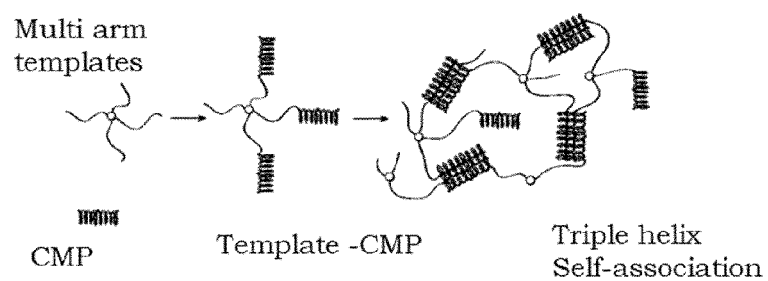
FIG. 3. Schematic showing the fabrication of hydrogels comprising an ECM mimetic peptide, in this case, a triple helical collagen mimetic peptide (CMP) and a polymer template, e.g. 4 armed PEG.

Collagen mimetic peptides (CMP) are short synthetic peptides (15-100 amino acids long, preferably 20-40 amino acids) with an inherent ability to adopt a triple helical fold similar to the natural collagen. CMP's have mainly been used as model systems for elucidating and understanding the formation and stability of triple helix in the natural collagens. In order to enhance CMP's ability to form nanofibers and hydrogels CMP may be connected to a template. Without being bound by theory the template may stabilize the triple helix of the CMP and thereby enhance the possible formation of higher order of assembly. The template may be a polymer or a co-polymer and may have at least two arms (such as 3, 4, 5 or 6 arms) or the templates may be a multiple branched molecule or polymer such as spider silk, hyperbranched polymers or dendrimers. In one embodiment the template is multiarm polyvinylchloride. In another embodiment the template may be a succinylated poly(N-isoacrylamide), e.g. polyethylene glycol (PEG), terpolymer of poly(N-isopropylacrylamide-coacrylic acid-coacryloxysuccinimide or PNiPAAm-coAAc-coASI. Preferably the template has two or more long chains, for example each chain may have a molecular weight of at least 5000 g/mol, or at least 15,000 g/mol. The arms or branches of the template comprise functional groups that may form secondary bonds such as hydrogen bonds or dipole-dipole bonds. FIG. 3 discloses CMP and templates and the formation of triple helix.

Multi-armed PEGs and PEG-collagen hydrogels have previously been reported as scaffolds for tissue engineering. PEG containing hydrogels have previously been shown to have fairly low elastic modulus, between 0.2-2 MPa for collagen-PEG hydrogels. Prior art has shown cell adhesion to said scaffolds with a preference for rough surfaces. Both PEG and PEG-collagen gels are susceptible to hydrolysis and PEG-collagen hydrogels are easily degraded by collagenase within 2 days. In one embodiment of the present invention the matrix material (the hydrogel) comprises a PEG with at least 3 arms, or at least 4 arms, or 8 arms, or a combination thereof. Addition of CMP, however, renders the hybrid resistant to collagenase and thereby more stable.

The present inventors have produced collagen or CMP hydrogels that are transparent (for example the light transmission may be at least 80%, or at least 85%, or preferably at least 90% for wave lengths between 400 and 700 nm, and with backscatter under 3%, as low as 1%). This transparency is important in certain applications such as intraocular lenses, cornea implants or prostheses etc., which has not been the case when hydrogels have been cross-linked with EDC.

The matrix material or the hydrogels of the present invention may be cross-linked via the functional groups of the first and the second polymer and optionally via cross-linking agents. In one embodiment the cross-link is a thio-ether as a result of a reaction between a methacrylate and a thiol group. In another embodiment the cross-link is a carbon-carbon bond for example as a result from a reaction between methacrylate or acrylate groups.

The matrix material or the hydrogel may further comprise cellulose, carboxymethyl cellulose (CMC) or silk. The addition of these polymers improves the mechanical properties for example the suturability.

In order to minimize the risk of damages to the eye or discomfortness the matrix material should preferably be as soft as possible, the elastic modulus may be less than 200 MPa, or less than 100 MPa or less than 50 MPa, or less than 10 MPa. The tensile strength of the hydrogel may be 1 MPa or more, or 3 MPa or more. The elongation at break may be more than 10%, or more than 20%, or more than 30%.

The Core Part

The core part is preferably arranged essentially in the middle of the matrix material and is transparent. The core monomers that are added to the matrix material are polymerized within the matrix material forming the core material, i.e. it forms an interpenetrating network (IPN) or the like together with the matrix material, and may be arranged to be exposed on both sides of the implant. The weight ratio of polymerized olefinic or UV polymerizable monomers (that are anti fouling) may be from 1 wt % to 95 wt % for example 1 wt % or more, or 5 wt % or more, or 15 wt % or more, or 30 wt % or more, or 50 wt % or more, or 95 wt % or less, or 85 wt % or less, or 75 wt % or less, or 65 wt % or less, or 55 wt % or less of the total weight of the core part. In one embodiment the ratio of polymerized olefinic or UV polymerizable monomers is 30-70 wt %, or 40-60 wt %. When the application is a cornea implant the amount of core monomers added is calculated to result in a core part having a diameter of 2-8 mm, or 3-5 mm. Any suitable initiator may be used for polymerizing the core monomers, preferably in an amount of 0.5-5 wt %, or 1-3 wt %.

The core monomers, and optionally an initiator and optionally the cross-linker may be added to the surface of the matrix material or injected into the matrix material or added to the matrix material in any other suitable way. The core monomers and the cross-linker are left to diffuse into the matrix material and optionally left to diffuse through the matrix material to the other side of the product. In one embodiment the core monomers and the cross-linker is left to diffuse into the hydrogel for at least 30 seconds or more, or 1 minute or more, or 5 minutes or more, or 15 minutes or more, or 2 hours or more, or 24 hours or more. In one embodiment the monomers are left to diffuse for 1 to 15 minutes. The core monomers are then left to cross-link preferably by applying UV radiation for at least 5 minutes, or at least 15 minutes. Preferably the core monomers are added in surplus and preferably the product is washed and rinsed after the cross-linking step. In order to obtain a core part in a limited area of the matrix material a mask may be used to cover the area where the core material is not wanted. In that way only core monomers that are within the desired limited area will be exposed to UV and polymerized.

The core monomers are preferably olefinic monomers susceptible to radical polymerisation. Non-limiting olefinic monomers are acrylated monomers such as methacrylate (MA), methyl methacrylate (MMA), methyl ether methacrylate (MEM), or hydroxyethyl methacrylate (HEMA), HEMA-poly ethylene glycol methacrylate (HEMA-PEGMA), HEMA-polyethylene glycol methyl ether methacrylate (HEMA-PEGMEM), 2-(2-methoxyethoxy)ethyl methacrylate ($MEO_2MA$) and hydroxyl-terminated oligo (ethylene glycol) methacrylate (HOEGMA) or alkenes such as propylene, butene, pentene, hexene, or cyclic alkenes such as styrene, or combinations or co-polymers thereof. Polypeptides, for example polylysine, may be used in the core material. The polypeptides may have anti-fouling or anti cell/vessel growth properties or they may be present in the core part above a concentration where they start to exhibit anti-fouling or anti cell/vessel growth properties. α-N-carboxyanhydride ring-opening polymerization (α-NCA ROP) enables the efficient generation of homopolypeptides or block copolypeptides possessing desired chemical functionality to a targeted molecular weight in a controlled manner. Polymerization can be initiated either by UV exposure or by amine groups present in the matrix material. Another core material is fouling resistant biomimetic poly(ethylene glycol) based grafted polymers. In one embodiment the core monomers is a mixture of polypeptides and olefinic monomers.

In order to minimize the risk of damages or discomfort to the eye the core part should preferably be as soft as possible. Since the core part according to the present invention partly contains a hydrogel, the core part is not rigid but soft and elastic. The elastic modulus of the core material may be less than 200 MPa, or less than 100 MPa or less than 50 MPa, or less than 10 MPa, depending on the chemical composition and/or the method of making the hydrogel. The tensile strength of the hydrogel may be 1 MPa or more, or 3 MPa or more. The elongation at break may be more than 10%, or more than 20%, or more than 30%, depending on the chemical composition and/or the method of making the hydrogel. The mechanical properties may be tailored in order to adopt them to the host tissue.

Surface Modifications

In order to tailor the properties of the product the surface of the hydrogel and/or the core material may be modified, patterned or coated for example by photografting, microcontact printing or other lithography, templating, molding or any other suitable technique. Pattern resolution goes from 0.01 μm up to 500 μm or more, and may comprise of one or more patterns modified areas on the hydrogel and/or the core material with same or different coating functionality. The pattern may be of any geometrical shape and be regular or irregular and may be continuous or discontinuous. For example the pattern may be in the shape or lines or dots, or dots making up a line. The lines may be aligned and/or parallel. The dots or the lines may have a maximum width or diameter of 10 nm or more, for example 500 nm or more, or 1 µm or more, or 20 µm or more, or 100 µm or more, for example 10-50 µm, or 20-40 µm. The width of the lines has shown to influence the cell proliferation, Example 10 and FIG. 13. The lines or dots may be spaced at a distance of 1 µm or more, or 20 µm or more, or 50 µm or more, for example 20-70 µm. The space between the lines or the dots may influence the cell proliferation and growth.

According to the present invention a surface compound is added to the hydrogel surface. The surface compound is selected from the group consisting of polyethylene glycol (PEG)-acrylate polymer/monomers, PEG-methacrylate polymer/monomers, other acrylate, methacrylate, carboxyl, amino, amide, epoxide, hydroxyl, cyano, nitride, sulfonamido, acetylenyl, alkene, esters like imidoesters(N-hydroxysuccinimide ester) or pentafluorophenol ester or other, azide, thiol, maleimide, functionalized PEG derivatives, bifunctional compounds, drugs, bioactive substances, biological molecules including proteins or peptides. In one embodiment the surface compound is selected from polyethylene glycol (PEG)-acrylate polymer/monomers and/or PEG-methacrylate polymer/monomers. In another embodiment the surface compounds are selected from fibronectin, entactin or vitronectin.

In one embodiment the surface is functionalized with a PEGMA coating prior to lithography or printing. This introduces MA onto the surface of any hydrogel to standardize the surface chemistry (monomers and/or other molecules bearing functional groups may be used in this approach). The surface functionalization by PEG-MA may be done on any biopolymer, and may be done without the addition of an initiator. The surface of the matrix material and/or the core material may be modified, coated and/or patterned with PEG-MA, N-hydroxysulfosuccinimide (NHS), polypeptides such as YIGSR, IKVAV, RGD, ECM proteins, fibronectine derived peptides, combinations of synergestic peptides, DGEA peptide from collagen, antibodies, glycosaminoglucans, motifs from growth factors, or pharmaceutically active substances.

Polyethylene glycol-methacrylate (PEGMA) may be applied to a hydrogel without the use of an initiator resulting in a less toxic product. The application is done by UV photo-grafting the PEGMA on a hydrogel or a protein film. This modification enables 1) standardizing surface properties of collagen hydrogels, 2) attachment of surface functional groups, 3) creation of physical barrier for contamination. To the inventors knowledge this has never been done before for a regenerative implant or a prosthesis produced with such a protecting/functional PEGMA layer. For in vitro applications a thin (tens of nm) initiator free PEGMA hydrogel may be arranged on top of the "main hydrogel" with a purpose of standardizing surface properties for contact printing or photolitho. This again has a clear technological advantage: e.g., no optimization is needed for printing of chemical/biomolecular compounds even if there are slight variations in the quality of "main hydrogel" material, or even if its composition is changed intentionally. Also, such PEGMA+functional monomer or attached protein/bioactive substance layer/pattern will locally stimulate/suppress adhesion of cells, guide them, whereas during the later stages of cell culture experiment the tissue-promoting properties of the "main hydrogel" will become dominant. In order to take advantage of such cell programming architecture, the bearing material (the "main hydrogel") should be preferably be stable, especially if one wants to create 3D models, so that it supports the desired morphology, shape and patterns during production, storing and cell culture/tissue application steps.

Figure 11:
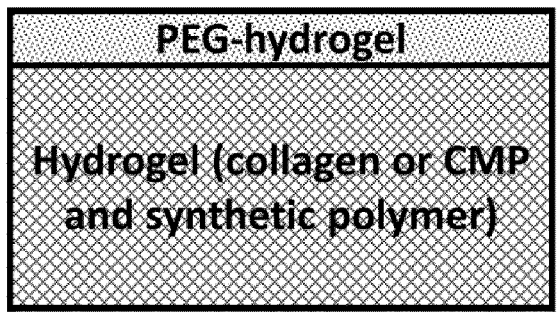
FIG. 11. Schematic structure of the obtained synthetic PEG hydrogel on top of a hydrogel according to the present invention.

The generalized resulting film structure as described above is shown in FIG. 11. This type of surface modification allows standardizing the chemical properties of the original protein and/or biosynthetic hydrogel film that, dependent on its composition, might display different number of surface chemical groups per surface area. This is advantageous for any further chemical modifications and functionalization including pattering of the surface (see below). In the implant device applications, such a modification makes it possible for the invention to be used as an additional barrier for exchange of different particles or viruses and bacteria between the implant and its surrounding tissue. Since the thickness of the barrier is very small, it will be degraded after some time after having performed its function. Further modifications of the photografted PEG hydrogel could be done, for example by microcontact printing of functional methacrylate monomers.

The present invention may be used in both in vitro and in vivo applications. For example the compound may be used for various implants such as but not limited to, cornea, cardiac patches, intraocular lenses, joints, and synovia, or in cosmetic surgery as a filling material such as breast implants or lip filling material, or as a anti-wrinkle material. The present invention may also be used as a drug-delivery vehicle, tissue glue or a barrier. The compound may further be used in vitro for example in chips, arrays, coatings or assays. The product according to the present invention may be used as a model or a model surface for studying cell migration or proliferation. The product may be coated on surfaces such as petri dishes or microwell plates in order to arrange cells in specific patterns or just as a cell growth support.

Method of Forming the Hydrogel

The hydrogels may be prepared by mixing a first and a second polymer or by mixing a first and a second solution where the first solution comprises the first polymer and the second solution comprises the second polymer. In one embodiment the pH of the first solution is less than 5, preferably less than 3, or more than 10, preferably more than 12. The first and the second solution may be prepared using water or purified water or any suitable buffer. In one embodiment the first polymer is methacrylated collagen or methacrylated CMP, and wherein the pH of the first solution is less than 5 or more than 10.

Without being bound by theory it is believed that the introduction of photochemically cross-linkable moieties into the first natural polymer will facilitate rapid and controllable intermolecular and intramolecular cross-linking leading to formation of a hydrogel. The cross-linking reactivity of the first natural polymer is enhanced by the incorporation of methacrylate and/or acrylate groups along its triple helical chain, which render it reactive towards nucleophilic attacks via Michael addition reaction. In addition, by being susceptible of radical formation under low-energy UV light irradiation, methacrylate groups offer another synthetic route to bridge collagen helices with a series of hydrophilic compounds (non-zero crosslinking). This modification makes the method presented herein very versatile for the synthesis of collagen/CMP-based hydrogels. The method according to the present invention may use UV in order to form cross-links or to speed up the cross-linking formation, for example UV 365 nm wavelength may be used for 5 to 15 min. In one embodiment a photoinitiator is used, for example at a concentration of 1-5% (w.r.t. to the first polymer). However, the method of preparing the present hydrogels does not require the use of UV, in one embodiment no UV is used.

When preparing the hydrogel the collagen or CMP concentration in the first solution may be 0.2 weight % or higher, or 0.5 weight % or higher, or 1 weight % or higher, or 2 weight % or higher, 5 weight % or higher, or 8 weight % or higher, or 12 weight % or higher, or 15 weight % or higher, up to 18 weight %.

When the hydrogel according to the present invention is prepared using CMP and a template the molar ratio between CMP and the template may be 10:1 to 1:10, such as 5:1 to 1:5, or 2:1 to 1:2.

The hydrogels may be prepared using a syringe mixing system. In a non-limiting example, a collagen (a first polymer) solution is placed into a syringe coupled to a second empty syringe through a 3-way T connector with septum at one end. Solutions of monomers/polymers (a second polymer/monomer) and photo initiator are then added sequentially from syringes via septum and mixed by pumping the combined solutions between the two main syringes. In one embodiment the injectable composition comprises a first and a second aqueous solution wherein the first solution is an aqueous solution comprising collagen or collagen mimetic peptide (CMP) comprising methacrylate and/or acrylate. The second solution is an aqueous solution comprising a synthetic polymer having two or more functional groups selected from thiol, acrylate and/or methacrylate functional groups. The polymer concentration in each solution is not more than 3 weight % in order to facilitate proper mixing and not too high viscosity. In one embodiment the composition further comprises cells and/or growth factors and/or cell nutrients.

The hydrogel may be prepared using a syringe mixing system. The syringe mixing system allows for a coupling reaction mostly in the localized regions where a concentrated aqueous collagen or CMP solution comes into contact with the crosslinking agents. In yet another embodiment the composition is arranged in a syringe wherein the first solution is arranged in a first compartment and the second solution in a second compartment.

The functionalizations of the natural and synthetic polymers and the system for forming hydrogels presented herein are also suitable as inks for 3D printing in order to prepare complex 3D structures, or for incorporating cells into the structure for example. The hydrogels of the present invention may be prepared together with cells, for example stem cells.

Amending the Conductivity of a Collagen Solution

The present inventors have found that the transparency of collagen or CMP based hydrogels can be controlled by manipulating the conductivity of collagen based solutions prior to further modification and/or crosslinking. The target conductivity is achieved by constant volume diafiltration.

The transparency of the cornea is critically dependent on the absence of any gaps in the matrix that are comparable in size to the wavelength of light, and on the presence of thin, parallel collagen fibrils In a non-limiting example a diafiltration system and membrane of choice is set-up as per the manufacturer's directions. A conductivity sensor is inserted into the permeate line as close as possible to the permeate exit port and the conductivity sensor is connected to a digital recording device. The collagen based solution is diafiltrated at constant volume using water (preferably sterile), USP (e.g. WFI) until the target conductivity is achieved. The processing data (permeate conductivity and temperature) are recorded every 60 seconds. The conductivity for each diavolume of permeate is noted.

For many collagen-based solutions and crosslinking methods the target conductivity to achieve hydrogels with optimized transparency has been found to be 45±5 µS/cm or 45±2 µS/cm. The target conductivity may be adjusted as required for alternative modifications and crosslinking methods.

The present method is applicable to all starting volumes of collagen based solutions. Ten to twenty diavolumes of water (preferably purified such as sterile for example USP water) is consumed to reach the above stated target conductivity. The temperature of the collagen solution throughout the process is preferably kept within 4 to 30° C., or 10 to 25° C., and must be controlled in a manner such that the temperature of the permeate passing thru the conductivity sensor is kept constant (±1° C., preferably ±0.5° C.) and within the calibration range (±1° C., preferably ±0.5° C.) of the sensor. The present inventors have found that if the temperature is not kept constant the correct conductivity of the solution will not be detected. The feed flow rate and feed pressure is dependent upon the diafiltration system used and may be adjusted in accordance with common practice. The present inventors have found that one feed flow rate that may be used is 1-10 LPM/m² (LPM means liters per minute), or 2-7 LPM/m², or 3-5 LPM/m² and a maximum feed pressure may be 10-35 PSI (69-241 kPa), or 15-30 PSI (103-207 kPa), or 20-25 PSI (138-172 kPa) or 25 PSI (172 kPa). The feed flow rate and feed pressure is preferably controlled in a manner that ensures a sufficient permeate flow rate thru the conductivity sensor. The present inventors have found that diafiltration time for 1 liter of a collagen based solution may be 8 to 10 hours. In one embodiment the diafiltrated solution is lyophilized followed by reconstitution of the collagen, i.e. making a new solution at any suitable concentration of the lyophilized collagen or CMP using water or any suitable buffer solution.

Light transmission and back-scattering measurements may be carried out at room temperature for white light (quartz-halogen lamp source) and for narrow spectral regions (centered at 450, 500, 550, 600 and 650 nm). In one embodiment a custom-built instrument was used to measure the percent transmission of samples as compared to open beam intensity. The relative percent of light back scattered from the collimated beam by the sample was measured with a circular array of 8 photodiodes, 30 degrees off axis.

The diafiltration also influences the mechanical properties which is clearly seen in Examples 11 and 12. By diafiltrating preferably prior to crosslinking the collagen the obtained hydrogel has a significantly higher elongation at break compared to non diafiltrated. The elastic modulus is also decreased indicating a softer hydrogel.

Applications

The present invention may be used as an implant itself or as part of an implant or as a vehicle for delivering active compounds such as drugs or growth factors, for example. The list of potential implants includes, but is not limited to, intraocular lenses, cornea, breast, lips, skin, or cardiac patches.

The inventors have been able to reproduce the morphology of the meshes found in decellularized dermis by electrospinning and plastic compression of porcine collagen alone or with other polymers (FIGS. 4A and B). However, to optimize the components of the dermal scaffold not only to support dermal fibroblasts but to allow for blood vessel in-growth, a soft fibrin hydrogel pre-seeded with EPCs may be incorporated to allow very rapid angiogenesis and allow for anastomosis formation, which is critical to successful grafting.

Although compressed fibrous meshes can be used as skin substitutes, a smooth substrate is more desirable for a smooth skin epidermis. The mesh may therefore be arranged within a hydrogel. Because of the cell friendly chemistry of the present hydrogel it is possible to incorporate cells (e.g. autologously harvested and expanded) into the fibrous mesh-hydrogel construction.

A cornea implant may have a thickness of 150-500 µm, such as 250-350 µm. The implant may be prepared by placing the hydrogel or the solutions forming the gel between two plates or molds having the desired thickness as a distance between the plates/molds. UV (for example 365 nm wavelength) may be applied for 5 to 20 minutes, such as 10-15 minutes.

CMP hydrogels have comparable mechanical properties to recombinant human collagen and are sufficiently robust for grafting as corneal implants, as shown in grafts into mini-pigs. Example 3 discloses certain properties of some CMP hydrogels.

The hydrogels according to the present invention may also be used in lab-on-a-chip systems, microscopy and microarray substrates, cell and tissue culture dishes, microwell plates, microfluidic and sampling, separation, purification, analytical tools. In this type of applications, the hydrogel can be used as an optimal support/environment for cell growth, proliferation, differentiation, tissue formation. Also, the hydrogel can be employed as a technical material for production of any kind of component for the above devices. The hydrogel can be used in the device as produced or it can be post-fabricated in order to obtain a specific shape, morphology, topography, stiffness, surface chemical, biochemical or physical properties, etc.

EXAMPLES

The present inventors have developed a non-limiting number of matrix materials preferably based on ECM macromolecules. Examples of collagen matrix materials are given below:

Example 1: Collagen Materials

A simple matrix material can be fabricated from carbodiimide crosslinked or epoxide or diepoxide, preferably BDDGE, crosslinked or UV crosslinked collagen/modified collagen as known in the art.

Example 2: Collagen Interpenetrating Networked Materials

These can be made from collagen-MPC or methcarylated collagen (MA) hybrid.

Collagen-MPC-co-PEGDA 0.5 ml of 15% (wt/wt) collagen aqueous solution was taken in the 3 way syringe system and thoroughly mixed with 150 µl of MES (2-(N-morpholino)ethane sulfonic acid) buffer in the syringe system. The pH of collagen solution was adjusted to pH 5±0.5 with 2M NaOH. After that calculated volume of 10% wt/vol of NHS was added followed by MPC solution and PEGDA solution in MES buffer. The Collagen:MPC ratios was 2:1 (wt/wt) and the MPC:PEGDA ratio was 3:1 (wt/wt). Then calculated volume of 4% (wt/vol) APS (ammonium persulfate) in MES and 2% (vol/vol) TEMED (Tetramethylethylenediamine) in MES were added subsequently to the syringe mixing system. The ratio of APS:MPC (wt/wt) was 0.03:1 and the ratio of APS:TEMED (wt/wt) was 1:0.77. Then calculated volume of EDC (5% wt/vol) was added. The molar ratio of Collagen-NH2:EDC was 1:0.7 and EDC:NHS was 2:1.

Collagen (MA)

0.3 mL (300 µL) of 5% MA-collagen (MAC) solution was taken in the 3 way syringe system and 300 µL of PEGDA and/HEMA containing 2% (w.r.tcollagen) Irgacure 2959 was added to the syringe and mixed well. The solution from the syringe was casted between two a glass slide/mould with spacers of desired thickness and exposed to UV 365 nm wavelength for 10 to 15 min.

Collagen-MPC-BDDGE 0.5 ml of 15% (wt/wt) collagen solution was loaded into a syringe mixing system and thoroughly mixed with 150 µl of Na-bicarbonate buffer in the syringe system. After that calculated volume of MPC solution and PEGDA solution in MES buffer was added. The Collagen:MPC ratios was 2:1 (wt/wt) and the MPC:PEGDA ratio was 3:1 (wt/wt). Then calculated volume of 8% (wt/vol) APS in MES and 6% (vol/vol) TEMED in MES were added subsequently to the syringe mixing system. The ratio of APS:MPC (wt/wt) was 0.03:1 and the ration of APS:TEMED (wt/wt) was 1:0.77. Then adequate amount of 2N NaOH was added to bring the pH at 11. Then calculated volume of BDDGE was added. The molar ratio of Collagen-NH2:BDDGE was 1:2.

Collagen-MPC interpenetrating networks (IPNs) have been previously described but there is no confirmation of that there is MPC in said networks.

The inventors of the present invention have shown that the addition of the MPC to a collagen network increased the elastic modulus the elongation at break in collagen hydrogels as shown in Table 1. In recombinant human collagen examples however a decrease in elastic modulus occurred, which correlated well to the increase in elasticity of the samples. Use of RHC instead of porcine collagen from previous data shows a 10-fold increase in tensile strength.

TABLE 1

Changes in mechanical properties of collagen versus collagen-MPC hydrogels.

|  | PC | PC-MPC | RHC | RHC-MPC | PC-MPC-BDDGE 1:2 | PC-MPC-BDDGE 1:4 |
|---|---|---|---|---|---|---|
| Tensile strength (MPa) | 0.15 | 0.12 | 1.7 | 1.29 | 0.10 | 0.15 |
| Elongation at break (%) | 14.57 | 21.29 | 13.88 | 37.89 | 16.41 | 12.88 |
| Young's elastic modulus (MPa) | 2.09 | 0.87 | 20.26 | 5.26 | 1.23 | 1.75 |

PC = Porcine Collagen
RHC = Recombinant Human Collagen

Example 3: Collagen Mimetic Peptide Hydrogels

Short bioactive peptide sequences that are cell-interactive have been used to mimic the properties of the holoprotein. Longer sequences, for example, collagen mimetic peptides (CMPs), are able to self-assemble and a range of these have been developed to model ECM-based peptides.

Figure 4:
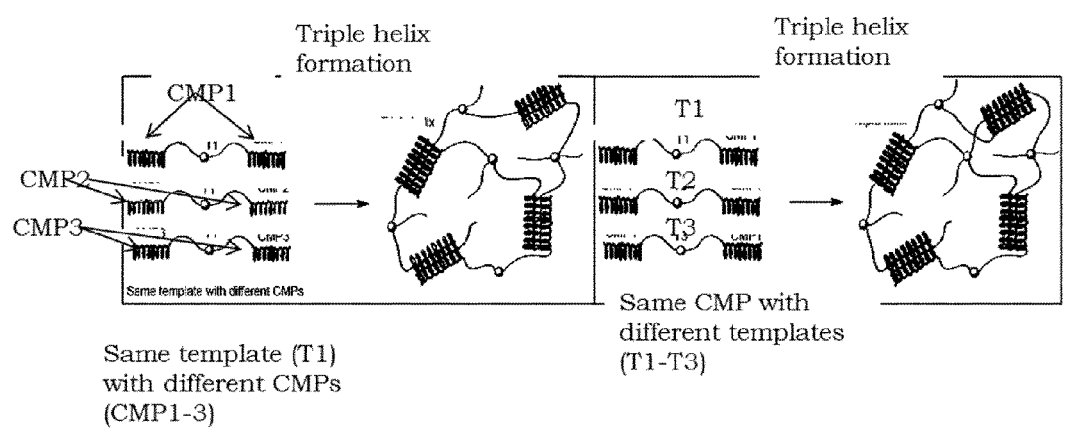
FIG. 4. Schematic for self assembling via hetero-dimerization.

In one example a 38 amino acid CMP and a long chain multiarm template (for example 4 arm/8 arm PEG, PNIPAAm, silk) was used to promote stepwise triple helical self assembly and form hydrogels, see FIGS. 3 and 4. Multiarm templates of appropriate lengths and flexibility will assist CMPs to self assemble into collagen-like triple helical network through well-defined self association; and will also provide the necessary backbone support to maintain the stiffness and mechanical strength to form self-supporting hydrogels. These biomaterials are highly designable, diversifiable with improved mechanical, optical and enzymatic properties. A series of such building blocks using different polymeric multiarm templates conjugated with CMPs or chimeric peptides comprising natural and synthetic ECM motifs or anti-microbial peptides can be produced. The combinations of such hetero moieties would give rise to multiple hybrid supramolecular assemblies mimicking natural ECM architecture, see FIG. 4, with tunable physical and biological properties.

Synthesis of Collagen Mimetic Peptide (CMP):

CMP's were synthesized on Symphony automated peptide synthesizer (Protein Technologies Inc.) using standard fluorenylmethoxycarbonyl (Fmoc) chemistry with HCTU (ChemPep Inc.) as the activating reagent. The synthesis was performed on a 0.1 mmol scale with Fmoc-PEG-PS resin (Applied Biosystems) using fourfold excess of amino acid in each coupling. The peptides were cleaved from the resin by treatment with a mixture of trifluoroacetic acid (TFA), water and triisopropylsilane (TIS) (95:2.5:2.5 v/v; 10 mL per gram of polymer) for 2 h at room temperature. After filtration, TFA was evaporated and the peptides were precipitated by the addition of cold diethyl ether, centrifuged and lyophilized. The crude products were purified by reversed-phase HPLC on a semi-preparative C-18 column (Grace Vydac) and identified from their MALDI-TOF spectra. The maximum at 225 nm and minimum near 200 nm are characteristic triple helical self assembly. The triple helical folding was found stable up to 40° C.

Synthesis of PEG-CMP:

Solution of CMP in water and solution of 8-Arm PEG-Maleimide in DMSO was mixed at the molar ratio of PEG-Maleimide:CMP=1:2.5 (Fig). After 4 days of continuous stirring the mixture was dialyzed through a dialysis membrane (12-14,000 molecular weight, Spectrum Laboratories, Inc., CA, US). After dialysis the solution was lyophilized to get solid PEG-CMP.

$^{1}$H spectra of 8-Arm PEG-Maleimide and PEG-CMP confirmed the conjugation of CMP with PEG-Maleimide. The complete disappearance of C=C Maleimide peaks (6.5-6.6) indicated the 100% conjugation of CMP with 8-Arm PEG-Maleimide.

Preparation of an Example of CMP Hydrogel

CMP hydrogel was prepared using a syringe mixing system as described in Invest Ophthalmol Vis Sci. 2006 May; 47(5):1869-75 which is hereby incorporated by reference. The solution of (12 weight %) CMP-PEG was cross-linked.

Figure 5:
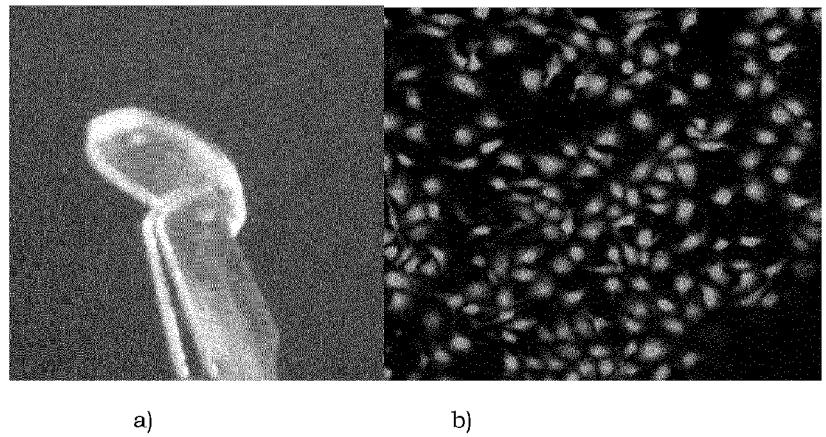
FIG. 5. (a) Matrix material implant made from collagen mimetic peptides (CMPs) templated on a multi-armed PEG backbone. (b) Corneal epithelial cells growing on the CMP-PEG hydrogel.

To fabricate CMP hydrogels, 0.5 mL aliquots of 12% (wt/wt) of CMP-PEG in aqueous solution was loaded into a syringe mixing system free of air bubbles. Calculated volumes of 1-ethyl-3-(3-dimethylaminopropyl) carbodiimide (EDC) (1.0 equimolar with respect to lysine $NH_2$ in CMP) and N-hydroxysuccinimide (NHS) (1.0 equivalence) solutions were added and thoroughly mixed at room temperature. The final solution was immediately dispensed as flat sheets or into curved polypropylene contact lens molds and cured at 100% humidity at 21° C. for up to 24 hours. The implants were washed three times with fresh 1×PBS prior to storage in PBS. FIG. 5A shows a CMP-based hydrogel, moulded as a corneal implant, with biocompatibility towards corneal cells (FIG. 5B).

The hydrogels of the present invention exhibit good elastic properties (i.e. high elongation at break), probably due to the presence of PEG. But the combination of CMP and PEG led to hydrogels that were biocompatible allowing host cells to grow and proliferate and showed a much higher elastic moduli (≥200 kPa) and were unexpectedly resistant to collagenase compared to other collagen-based materials (FIG. 6), making it an excellent candidate for a prosthesis that needs to retain its form to function.

Central Polymer (Optical) Core

This is the "core" of the invention, the ability to convert a regular corneal implant into a prosthesis. For example a methacrylate (MA) solution with UV initiator Irgacure 2959 (2 weight %) is added to the MPC-collagen hydrogel. Preferably the MA is allowed to diffuse into the hydrogel for at least 30 seconds or more, or 1 minute or more, or 5 minutes or more, or 15 minutes or more, or 2 hours or more, or 24 hours or more. The time interval allows for conversion of an implant from a regenerative implant to a prosthesis during surgery. Generally the gels were exposed to UV-A at 360 nm for 15 mins to form an optical core.

Example 4: RPro with Methyl Methacrylate (MMA) Core

Figure 8:
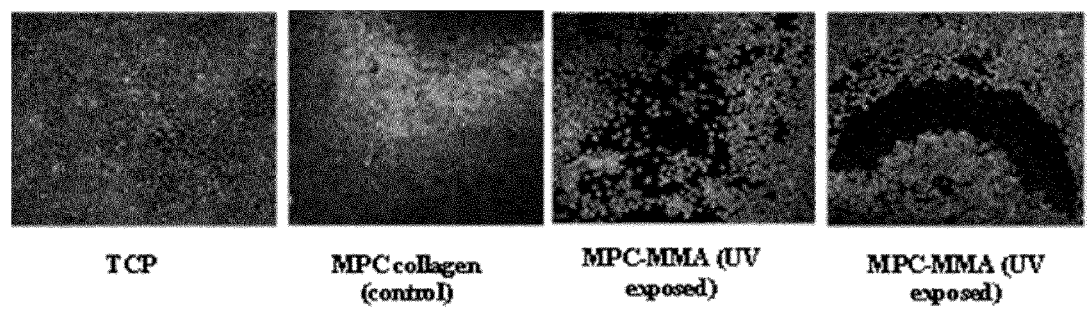
FIG. 8. Corneal epithelial cell culture on the MPC-MMA surface (images taken after 3 days of culture).

Collagen-MPC hydrogels were prepared as described above. MMA (methyl methacrylate) solution with UV initiator Irgacure 2959 (2 weight %) was added at the center of MPC collagen hydrogel at an amount saturating the matrix material and incubated it for 2 days for the diffusion of MMA into MPC-collagen gels. The gels were exposed to UV at 360 nm for 15 mins. The resulting RRro is shown in FIG. 7. Human corneal epithelial cells were seeded on the top of the scaffold and cell images were shown in FIG. 8.

Example 5: RPro with Poly-Hydroxyethyl Methacrylate (pHEMA) Core

Collagen-MPC prosthesis with pHEMA central core was prepared from HEMA using the procedure described in 1. HEMA (hydroxyethyl methacrylate) solution with UV initiator Irgacure (2 weight %) was added at the centre of MPC collagen hydrogel at an amount saturating the matrix material and incubated it for 5-10 mins for the diffusion of HEMA into MPC gels. Gels were exposed to UV at 360 nm for 15 mins. HEMA diffuses into MPC gels and whole centre has been polymerized but on its own, a pHEMA core is transparent.

Example 6: RPro with pHEMA-Poly-Ethylene Glycol Methacrylate (PEGMA) Core

Collagen-MPC prosthesis with (pHEMA-PEGMA) central core was prepared using the same procedure described in 1. HEMA-PEGMA (Poly-ethylene glycol methacrylate) HEMA-PEGMA solution with UV initiator Irgacure (2 weight %) was added at the centre of MPC collagen hydrogel at an amount saturating the matrix material and incubated it for 15 mins for the diffusion of HEMA-PEGMA into MPC gels. Gels were exposed to UV at 360 nm for 15 mins. 1:1 ratio of HEMA+PEGMA was polymerized in the centre of MPC gels. The polymerized part in the centre was transparent and stable for months.

Example 7: RPro with pHEMA-PEGMEM Core

Figure 9:
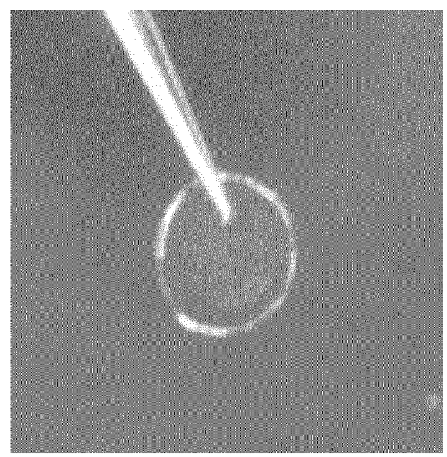
FIG. 9. RPro with pHEMA-PEGMEM core.
Figure 10:
FIG. 10. CMP (collagen mimetic peptide) RPro with pHEMA-PEGMEM core.

Collagen-MPC prosthesis with pHEMA-PEGMEM (MEM is methyl ether methacrylate) central core was prepared using the same procedure described in 1. HEMA-PEGMEM (1:1) solution with UV initiator Irgacure (2 weight %) was added at the centre of MPC collagen hydrogel and incubated it for 15 mins for the diffusion of HEMA-PEGMEM into MPC gels. Gels are exposed to UV at 360 nm for 15 mins. 1:1 ratio of HEMA+PEGMEM was polymerized in the centre of MPC gels. The polymerized part in the centre is transparent (FIGS. 9 and 10) and it is stable for months.

Example 8: Collagen Mimetic Peptide (CMP) RPro with pHEMA-PEGMEM Core

CMP prosthesis with pHEMA-PEGMEM (MEM is methyl ether methacrylate) central core was prepared using the same procedure described in 1. HEMA-PEGMEM (1:1) solution with UV initiator Irgacure (2 weight %) was added at the centre of CMP hydrogel and incubated it for 15 mins for the diffusion of HEMA-PEGMEM into MPC gels. Gels are exposed to UV at 360 nm for 15 mins. 1:1 ratio of HEMA+PEGMEM was polymerized in the centre of MPC gels. The polymerized part in the centre is transparent (FIGS. 9 and 10) and it is stable for months.

Surface Coating, Printing or Patterning

Example 9: PEG-MA Coating

Synthetic collagen photografting to the collagen surface was performed by adding a drop of 240 mM concentration of aqueous monomer solution of HEMA:PEGMA (1:1) was applied to the sample and pressed by a freestanding quartz disc. Subsequent irradiation with UV light (11 W) for 3 minutes gave a 20-25 nm PEG-hydrogel layer on the top of collagen surface (FIG. 11, as evidenced by atomic force microscopy analysis (AFM).

Figure 12:
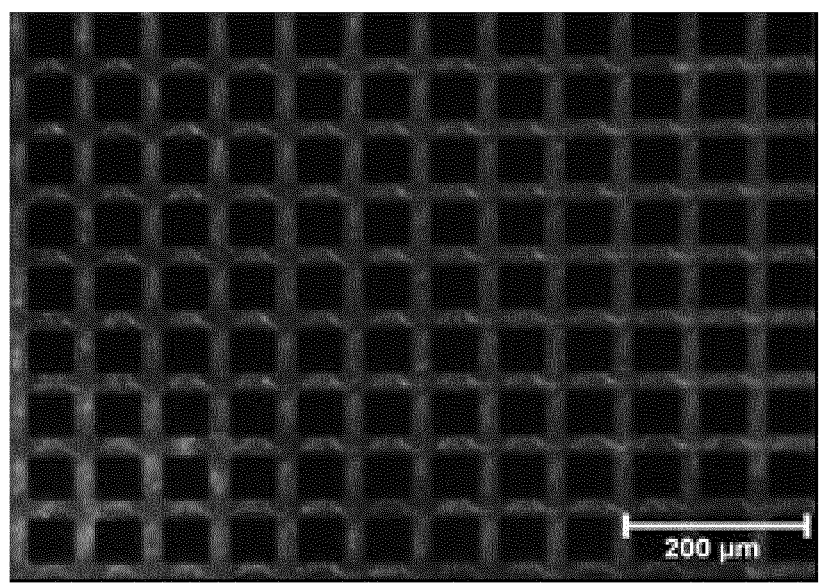
FIG. 12. Fluorescence micrograph showing visualization of a biotin-terminated pattern on a hydrogel surface containing layers as shown in FIG. 11.

Further modifications of the photografted PEG hydrogel could be done, for example by microcontact printing of functional methacrylate monomers. They were subsequently crosslinked with the PEG hydrogel (on-top of the original protein film) by additional irradiation with UV light. The present inventors have microcontact printed aminoethyl-methacrylate (AEMA), fibronectin and streptavidin that generated an amino group-containing pattern on otherwise chemically inert PEG hydrogel surfaces. Furthermore the surface was biotinylated via coupling NHS-biotin conjugate. Finally, the resulting pattern was visualized by streptavidin-coated quantum dots (FIG. 12).

Example 10: Microcontact Printing with Fibronectin "Ink"

Recombinant human collagen type III (RHCIII)-MPC hydrogel samples, 500 μm thick, were washed using 0.1 M PBS buffer pH 5.7 and dried under a nitrogen gas (N2) stream prior to use. Free carbonyl groups on the collagen surfaces were activated using 1 ml of 2.5 mM N-hydroxysulfosuccinimide (NHS) and 10 mM ethyl-N'-(3-dimethyl-aminopropyl)carbodiimide (EDC) solution (PBS, pH=5.7) for 15 min. All samples were rinsed for 30 s in fresh PBS buffer (pH=5.7) and dried with N2 just before printing.

Stamps (5 mm×5 mm) of poly(dimethylsiloxane) (PDMS) were prepared using a previously published protocol. To examine attachment and proliferation of single corneal epithelial cells, a pattern that comprised 30 μm wide lines separated by 60 μm spaces in between was used. To examine the attachment and spread of multiple cells, 200 μm wide lines, separated by 200 μm spaces were tested. For printing, the PDMS stamps were thoroughly rinsed in ethanol, dried in a stream of nitrogen gas and treated with oxygen plasma (intensity 20 W) for 30 s in plasma dry cleaner (Femto, Diener Electronic GmbH, Ebhausen, Germany). The stamps were then coated with "ink", in this example, comprising a 10 μL solution containing of fibronectin 0.5 mg/ml and 2 μg/ml BSA-TR® in PBS buffer, pH 8.0. After 10 min. at room temperature, the stamps were rinsed in water for 20 s and dried for 1 min. under a nitrogen gas stream.

Figure 13:
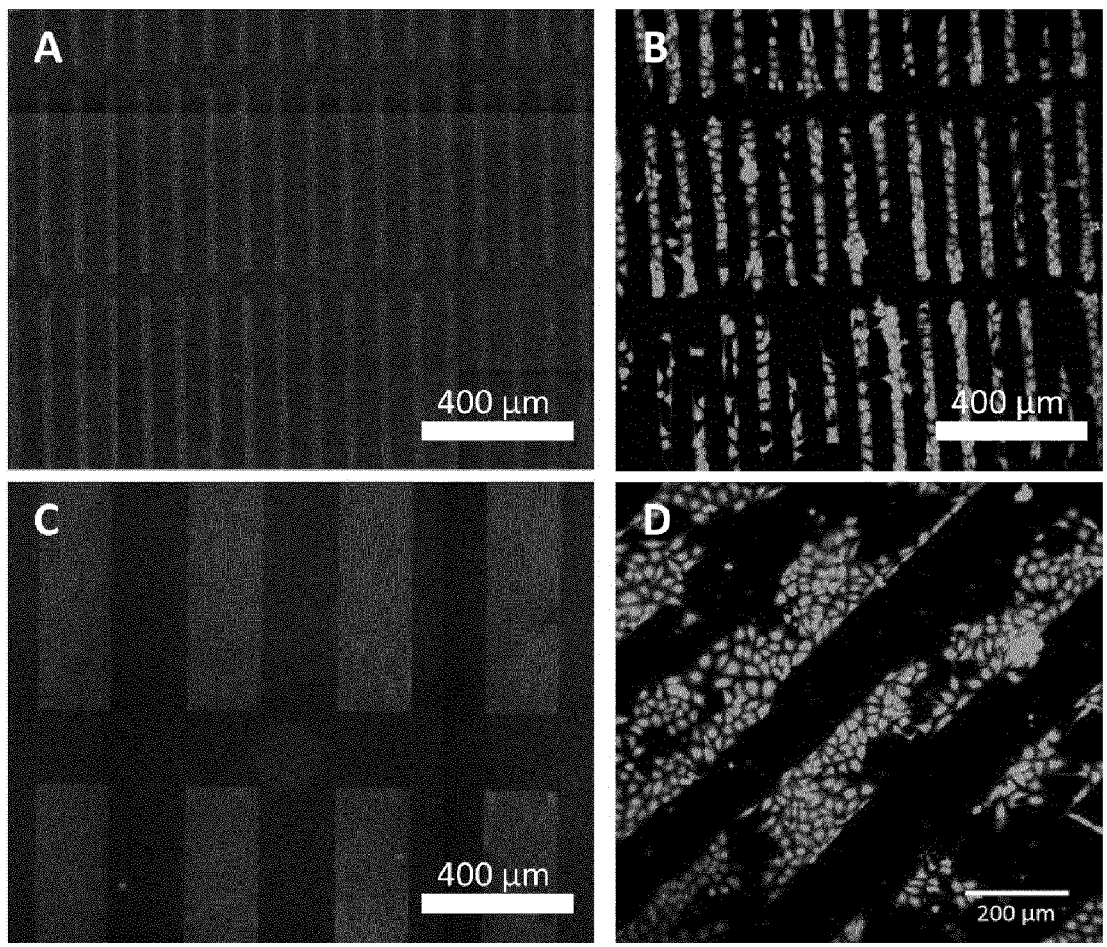
FIG. 13. a) Human fibronectin (traces of BSA-TR®) patterns on MPC collagen hydrogel: the line width 30 μm, space in-between 60 μm. b) Corneal epithelium cells on 30 μm-wide line patterns on MPC collagen hydrogel. c) Human fibronectin (trace of BSA-TR®) patterns on MPC collagen, the line width 200 μm, spacing 200 μm. d) Corneal epithelium cells on 200 μm line patterns on MPC collagen.
Figure 14:
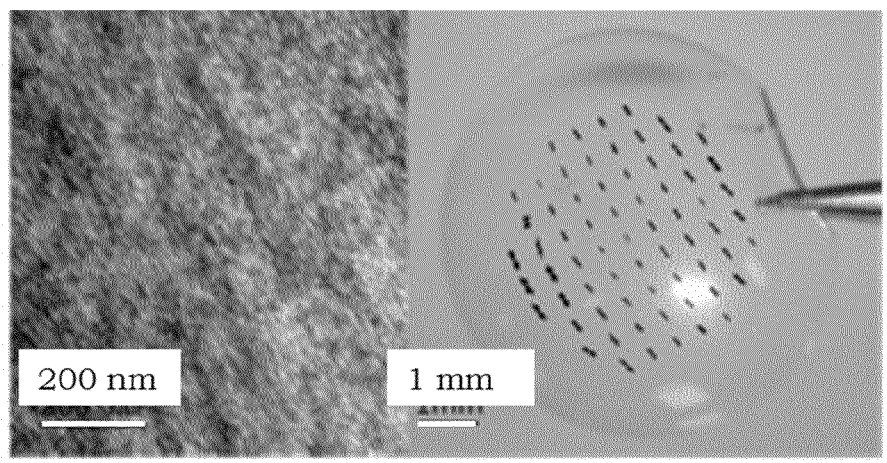
FIG. 14. A) To the left, transmission electron micrograph of an RHCIII-MPC hydrogel examined following high pressure freezing, The image shows a predominantly uniaxial orientation of very fine collagen filaments. Right: The direction of preferentially aligned collagen from the same specimen, as determined by x-ray scattering, has been superimposed onto an image of the hydrogel. The data confirms that a predominantly uniaxial alignment of collagen exists throughout the hydrogel. B) Schematic figure of a hydrogel surface according to the present invention with aligned collagen fibrils.
Figure 14:
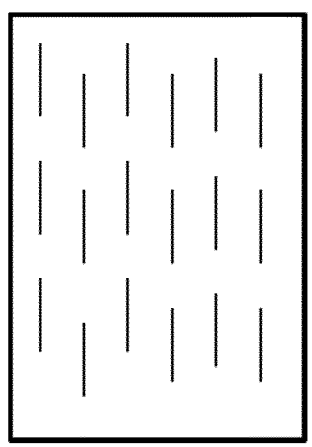

Activated RHCIII-MPC surfaces were then contact-printed for 5 min. The stamp was then removed and patterned RHCIII-MPC hydrogel surface was layered with a blocking solution containing 10 mM (PEG)3NH$_2$ in PBS buffer pH8.0 for 40 min. After incubation, the surfaces were carefully washed several times with fresh PBS buffer pH7.4 and are ready for use or stored in buffer solution until used, for example for seeding cells. FIG. 13 shows examples of fibronectin patterned surfaces and cells.

Diafiltration of Collagen

Example 11

Method

RHC III (bulk acidic solution) was diafiltrated until the conductivity of the permeate was 45 μS. Note: this was changed from our earlier method in which the end point was 40 μS.

The diafiltrated bulk acidic solution was lyophilized in house.

All implants were made in 0.05 MMES that was filtered thru a 0.2 μm filter.

The EDC:primary amine ratio was 0.4 (EDC:NHS ration was 1:1).

Starting volume was 0.4 ml.

Total dilution was 150 μl (from the T-piece)+24.5 μl (EDC)+14.7 μl (NHS)=189.2 μl resulting in a final collagen content of approximately 12.6%

TABLE 2

Characterization.

| Characterization | Human Cornea | 15% RHCII Formulation | Prebious 13.7% RHCII Formulation |
|---|---|---|---|
| Optical properties | | | |
| Transmission | >85% | n/a | 89.8 ± .9% |
| Backscatter | 6-8% | | 0.81% |
| Refractive Index | 1.3375 | 1.358 ± 0.0015 | 1.35 |
| Thermodynamic properties | | | |
| DSC (° C.) | 65.1 | 57.82 | 58.6 |
| Mechanical properties | | | |
| Tensile strenght (Mpa) | 3.8 | 1.439 ± 0.094 | 1.700 ± 0.205 |
| Modulus (Mpa) | 3-13 | 8.82 ± 2.18 | 20.26 ± 2.04 |
| % Breaking Strain | — | 23.01 ± 3.47 | 13.89 ± 0.69 |
| % Water content | 80% | 90.5 ± 3.58% | 90% |
| TEM | n/a | n/a | n/a |

TABLE 2-continued

| Characterization | | | |
|---|---|---|---|
| Characterization | Human Cornea | 15% RHCII Formulation | Prebious 13.7% RHCII Formulation |
| In vitro Biocompatibility | | Supports epithelial cell proliferation and stratification | Supports epithelial cell proliferation and stratification |

Note:
Water content based on drying down an intact 500 μm implant.

The collagenase degradation profile for 15% RHC III as compared to 13.7% RHC III at equivalent crosslinking rations is given below. All material was made using a permeate conductivity cut-off of 45 μS.

RHC=Recombinant Human Collagen

Example 12

Method
Diafiltration of 2 batches of RHC III bulk acidic solution
Batch 1: Final permeate conductivity=40 μs
Batch 2: Final permeate conductivity=45 μs
RHC Gels were made with EDC:primary amine ratio of 0.4 (EDC:NHS ratio was 1:1)
Results

TABLE 3

| Mechanical properties | | |
|---|---|---|
| Mechanical properties | Permeate = 40 μS | Permeate = 45 μS |
| Tebsile strength (MPa) | 1.700 ± 0.205 | 2.02 ± 0.319 |
| Modulus (MPa) | 20.26 ± 2.04 | 9.639 ± 1.700 |
| % Breaking Strain | 13.89 ± 0.69 | 32.68 ± 1.77 |

Example 13—Hydrogel of MAC and PEG-SH

A hydrogel from the Michael addition reaction was prepared by mixing 0.5 mL of 10 wt % MAC with a 4-arm PEG thiol using a three way syringe system. The PEG thiol was dissolved in water and added to get the overall concentration of methacrylated collagen of 5%. The solution from the syringe was casted between two glass slides/molds with spacers of desired thickness and stored under humid conditions overnight. A stiff hydrogel was obtained. This result confirms the proof-of-concept that a stiff hydrogel can be prepared by the overnight reaction of MAC with a 4 arm PEG thiol. The absence of UV light and by-products makes this hydrogel promising for corneal application. Such features make this hydrogel suitable for encapsulation and delivery of stromal stem cells in cases of HSV conditions, when the patient lacks the pool of the stem cells, thus making conventional regenerative approaches impractical.

Hydrogels

Example 14—Methacrylation of Collagen 0.5% collagen solution in 1×PBS was prepared (pH 6.5-6.7). The pH was raised to 10 using NaOH at −4° C. Methacrylic anhydride (10:1 molar ratio w.r.t. amine groups in collagen) was added drop wise to collagen solution in 3 batches and the solution was stirred vigorously for 4 hours. The reaction mixture was dialyzed for 4 days against distilled water at room temperature.

The results were analysed using circular dichroism and NMR.

The circular dichroism spectrum of MAC at 1% by weight concentration in Milli-Q water, at room temperature, showed maximum at 225 nm and a minimum near 200 nm at pH 7.4 and pH 10 which is indicative of collagen triple helices. The triple helical propensity is higher at high pH.

HNMR spectra of MAC at 1% by weight concentration in $D_2O$, at room temperature showed two new peaks between 5-6 ppm, characteristic for two acrylic protons of methacrylic functionality.

The inventors found that transparency was achieved by varying the pH of methacrylated collagen (MAC) in water. MAC was transparent if the pH was either less than 5 or above 10. This is something not reported before.

Example 15: Formation of Hydrogel with MAC and Acrylate Monomers

The example relates to mixing of MA-collagen with acrylate monomers to form multicomponent gel 0.3 mL (300 μL) of 5% MA-collagen (MAC) solution was taken in the 3 way syringe system and 300 μL of polyethylene glycol-diacrylate (PEGDA), PEG methacrylate (PEGMA), hydroxyethyl methacrylate (HEMA), polyethylene glycol methyl ether methacrylate (PEGMEM) containing 2% (w.r.t collagen) Irgacure 2959 was added to the syringe and mixed well. The solution from the syringe was casted between two glass slides/molds with spacers of desired thickness and exposed to UV 365 nm wavelength for 10 to 15 min.

TABLE 4

| Experimental set up. | | |
|---|---|---|
| MAC | Acrylate monomer | Ratio (mol) |
| 300 μL | 300 μL | 1:1 |

The example relates to mixing of MA-collagen with multiple acrylate monomers to form multicomponent gel 300 μL of 5% MA-collagen was mixed with two different acrylate monomers e.g. (HEMA+PEGDA) with 2% (w.r.t collagen) Irgacure 2959 and mixed well. The solution from the syringe was casted between two glass slides/molds with spacers of desired thickness and exposed to UV 365 nm wavelength for 10 to 15 min.

TABLE 5

| Experimental set up. | | | |
|---|---|---|---|
| MAC | HEMA | PEGDA | Ratio |
| 300 μL | 150 μL | 150 μL | 1:0.5:0.5 |

The hydrogel was analysed with DSC. It showed that the hydrogel comprises at least two polymer networks with $T_{g1}$ and $T_{g2}$ of 44.7 and 56.3° C., respectively. A third step is visible in the curve, but further studies are needed to confirm the presence of a three-polymer hydrogel.

Example 16—Preparation of CMP Hydrogel

T-piece mixing system was used to make hydrogels with CMP, which was previously described. For making the hydrogel 500 mg of 12% (w/w) CMP was mixed with 300

μl of water. Calculated volumes of NHS and then EDC were added to the syringe mixing system. Depending on the molar equivalent ratio of EDC to amine of CMP, 3 different types of hydrogel were made; CMP-NH$_2$:EDC=1:0.5, CMP-NH$_2$: EDC=1:1 and CMP-NH$_2$:EDC=1:2. The molar ratio of EDC:NHS was 1:1. The stock solution concentrations of EDC and NHS were adjusted in such a way that in all different types of hydrogels, dilution factor of CMP remained same. All addition followed by thorough mixing. Table 6 and 7 discloses some results and properties of the obtained hydrogels. Circular dichroism revealed triple helical formation.

TABLE 6

Mechanical properties of CMP hydrogels.

| Formulation CMP:EDC/NHS ratio | Tensile strength/max Load (kPa) | Elongation at Break (%) | Young's Modulus (mPa) |
|---|---|---|---|
| 1:0.5 | 1.47 ± 1.2 | 67.10 ± 37.20 | 0.22 ± 0.05 |
| 1:1 | 1.79 ± 0.5 | 64.02 ± 8.09 | 0.21 ± 0.08 |
| 1:2 | 0.99 ± 0.3 | 30.04 ± 7.42 | 0.26 ± 0.04 |

TABLE 7

Water content of CMP hydrogels.

| Formulation | Initial Wt | 1 h drying | Water Content (%) | 24 h drying | Water Content |
|---|---|---|---|---|---|
| CMP 1:1 | 45.9 | 20.6 | 55% | 3.2 | 93% |
| CMP 1:1 | 39.4 | 16.6 | 58% | 3 | 92% |
| CMP 1:2 | 49.3 | 23.5 | 52% | 4.9 | 90% |
| CMP 1:2 | 48.3 | 22.2 | 54% | 4.3 | 91% |

Example 17—In Vivo Study of CMP Hydrogel

Figure 6:
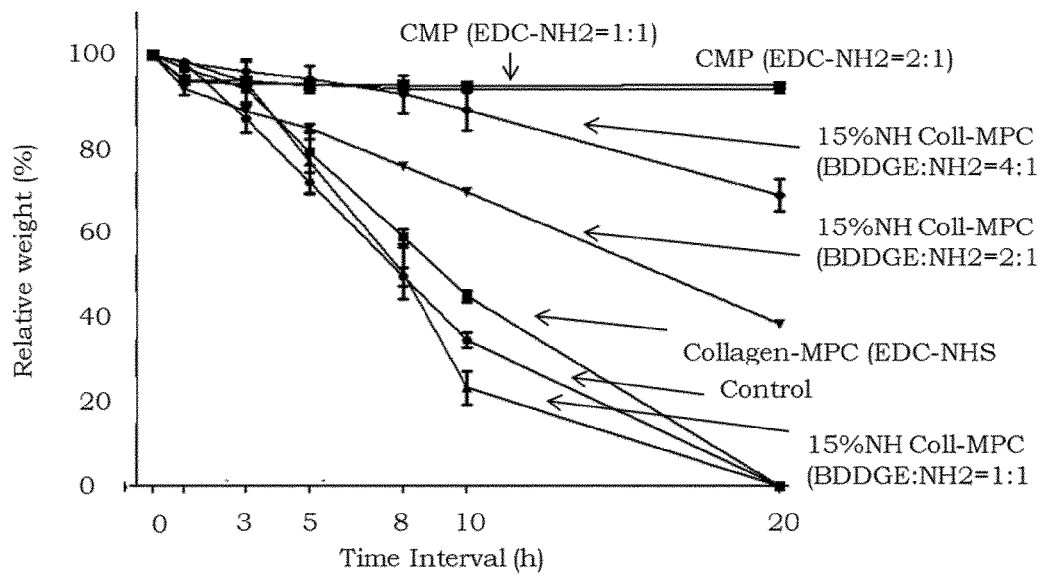
FIG. 6. Digestion of matrix material hydrogels by collagenase, showing that CMP-PEG hydrogel is resistant to enzymatix digestion.

The CMP-EDC 1:2 hydrogel was tested in vivo in a pig. Cornea shaped implants were implanted into the eyes of three pigs and regular analysis were conducted. As positive control collagen based hydrogel was used and the results from the CMP hydrogel have so far been as good as for the collagen. CMP hydrogels integrates into the host tissue and discloses epithelial regeneration after 2 weeks already. After 3 months the sensitivity of the eye was restored together with the tear formation function. After 9 months nerves were regenerated. The stability of the hydrogel is seen in FIG. 6.

Example 18

Materials

All inorganic salts and basic chemicals were of analytical grade and purchased from Sigma-Aldrich (St. Louis, Mo. and Steinheim, Germany), Carl Roth GmbH (Karlsruhe, Germany) or Merck KGaA (Darmstadt, Germany) unless otherwise stated. Research grade RHCIII, produced in yeast (*Pishia pistoris*), was purchased from 3H Biomedical (Uppsala, Sweden) and Fibrogen (San Francisco, Calif.). N-(3-dimethylaminopropyl)-N'-ethylcarbodiimide (EDC), N-hydroxysuccinimide (NHS), 2-morpholinoethane sulfonic acid Monohydrate (MES), Poly(ethylene glycol) diacrylate (PEGDA, Mn=575), Ammonium persulphate (APS) and N,N,N,N-tetramethylethylenediamine (TEMED) were obtained from Sigma-Aldrich (MO, USA). 2-methacryloyloxyethylphosphorylcholine (MPC) was obtained from Biocompatibles (UK) and Paramount Fine Chemicals Co. Ltd. (Dalian, China).

Recombinant Human Collagen Phosphorylcholine Hydrogels

RHCIII-MPC hydrogels were produced as we previously published [15] but with a range of different starting concentrations of RHCIII to select an optimal formulation for laser profiling and μCP. Briefly, a 450-500 mg of RHCIII solution of one of a range of starting concentrations (13.7 (w/w) %, 18 (w/w) % or 20 (w/w) %) was buffered with 150 μl of 0.625 M MES buffer within a syringe mixing system in an ice-water bath. 200 μl MPC solution in 0.625 M MES was added into the mixing system. The MPC:RHCIII (w/w) ratios used with either 1:4, 1:2 or 1:1. PEGDA was then added by a microsyringe (PEGDA:MPC (w/w)=1:3). Calculated volumes of 4% (w/v) APS solution in MES and 2% (v/v) TEMED solution in MES were added sequentially (APS/MPC (w/w)=0.015:1, APS:TEMED (w/w) 1:0.77). After thoroughly mixing, calculated amounts of NHS (10% (w/v) in MES) and EDC (5% (w/v) in MES) solutions were added and the reactants were thoroughly mixed at 0° C. (EDC:RHCIII-NH2 (mol:mol)=0.3-1.5:1, EDC:NHS (mol:mol)=1:1). The final mixed solution was immediately cast into cornea-shaped moulds (12 mm diameter, 500 μm thick) or between two glass plates with 500 μm spacers. The hydrogels were cured overnight at 100% humidity under nitrogen at room temperature. The cornea-shaped implants were cured for an additional 5 h at 37° C. After demoulding, they were washed thoroughly with 10 mM phosphate buffered saline (PBS) and then stored in PBS containing 1% chloroform to maintain sterility.

Characterization of Hydrogels

All samples were tested in triplicate. The water content of RHCIII-MPC hydrogels was determined by weighing samples that were blotted dry to remove surface liquid to obtain the wet weight (W0). These pre-weighed hydrogels were then dried at room temperature under vacuum to constant weight, which is the dry weight (W). The equilibrated water content of hydrogels (Wt %) was obtained according to the following equation: Wt %=(W0−W)/W0× 100%.

Optical properties of the resulting hydrogels were characterised by obtaining the refractive indices (RIs) of 500 μm flat, fully hydrated hydrogels equilibrated in PBS using an Abbe refractometer (Model C10, VEE GEE Scientific Inc., Kirkland, Wash.) at 21° C. with bromonaphthalene as the calibration agent. Light transmission and back-scattering measurements were carried out at 21° C. on a custom-built instrument equipped with a quartz halogen lamp for white light measurements as previously reported [24]. The percentage light transmission through the hydrogels was compared to the open beam intensity. The amount of backscattered light (%) from each sample was measured by the circular array of eight built-in photodiodes, angled at 30 degrees off axis.

The mechanical properties (tensile strength, moduli and elongation at break) were determined using an Instron mechanical universal tester (Model 3342, Instron, Canton, Mass.) equipped with a 0.01 kN load cell and Instron Series IX/S software. Flat hydrogels (12 mm×5 mm rectangular strips, 0.44 mm thick) were measured. The gauge length of each specimen tested was 5 mm. The crosshead speed was 10 mm min−1 and the sampling rate was 10 points s−1. Implants were not pre-stressed. Measurements were taken at room temperature.

The morphology of the RHCIII-MPC hydrogels compared to human corneas and RHCIII hydrogels alone was examined using scanning electron microscopy (SEM). All samples were lyophilized to minimize the shrinkage of the human cornea and collagen scaffolds due to the vacuum applied during freeze-drying and SEM imaging. Briefly, PBS-equilibrated samples of each construct or human eye bank corneas were frozen over night at −80° C. and then placed in the drying chamber of a lyophilizer at a condenser temperature of −40° C. and vacuum pressure of 0.8 Torr and dried for 7 hrs. The scaffolds did not collapse through the process while there was some degree of shrinkage for all test samples, e.g. 40% for human cornea and 50% for the biosynthetic collagen hydrogels due to the applied vacuum. The samples were then cut using a sharp surgical knife at a vertical angle to minimize the changes in the scaffolds' structure due to the cut and attached onto metal holders using conductive double-sided tape, and sputter coated with a gold layer for 60 seconds at 0.1 bar vacuum pressure (Cressington Sputter Coater 108) prior to SEM examination. SEM micrographs were taken at 25 kV at various magnifications on a scanning electron microscope (Model S-2250N, Hitachi, Japan). Comparisons were made against human eye bank corneas prepared in the same way.

Precision Laser Cutting of the Hydrogels and Tissue Welding

Laser trephination (or cutting) of three cornea-shaped RHCIII-MPC hydrogels (12 mm in diameter and 500 µm thick) was carried out using a femtosecond laser (IntraLase™ FS Laser, Abott Medical Optics, Abbott Park, Ill., USA). The laser was set to cut out a top-hat shaped implant from the hydrogel (one of the more common configurations for laser-assisted tissue trephination).

The cutting parameters used were 6.0 mm diameter of the anterior side cut, 8.0 mm diameter of the posterior side cut, and a depth of 250 µm for the lamellar cut. The energy for the ring lamellar cut, anterior side cut and posterior side cut were 2.80 µJ, 1.50 µJ and 1.50 µJ, respectively. For implant/tissue welding, matched complementary cuts were also made on excised porcine corneas (obtained from an abattoir) and RHCIII-MPC implants using the femtosecond laser (Wave Light GmbH Erlangen, Germany). RHC-MPCIII implants inserted into the matched donor cornea bed were welded together using standard riboflavin/dextran crosslinking techniques (1% riboflavin, 365 nm, 3 mW/cm$^2$, 30 min.) [25] using a MLase UV crosslinking device (MLase AG, Germering, Germany).

Microcontact Printing on Hydrogels

RHCIII-MPC hydrogels containing 18% RHCIII, with RHCIII:MPC=2:1 and EDC:RHCIII-NH2 (mol:mol)=0.4:1 were used for all µCP. Flat-cast hydrogels were cut into approximately 2 cm×2 cm×500 µm pieces and washed with 0.1 M PBS, pH 5.7 and dried under a nitrogen gas (N2) stream prior to use. Free native carboxyl groups from the hydrogel surface were activated by immersing the samples in 2 ml of the PBS (pH 5.7) solution containing 10 mM EDC and 2.5 mM NHS for 15 min. All samples were rinsed for 30 s in fresh PBS buffer and dried with N2 gas just before printing.

Square 1.5 cm×1.5 cm poly(dimethylsiloxane) (PDMS) (Dow Corning, Midland, Mich., USA) stamps were prepared using a previously published protocol [26]. To examine the attachment and proliferation of single human corneal epithelial cells, a stamp that comprised 30 µm-wide protruding stripes separated by 60 µm spaces was designed. To examine the attachment and spread of multiple cells, 200 µm-wide stripes, separated by 200 µm spaces were tested. Prior to printing, the PDMS stamps were thoroughly rinsed in ethanol, dried under a stream of nitrogen gas and treated with oxygen plasma (20 W power) for 30 s in plasma dry cleaner (Femto, Diener Electronic GmbH, Ebhausen, Germany).

The stamps were then pre-loaded with "ink" comprising a 30 µL solution of 0.5 mg/ml human fibronectin (FN) (Yo Proteins AB, Huddinge, Sweden) with 2 µg/ml bovine serum albumin conjugated with fluorescent Texas Red (BSA-TR®; Invitrogen, Eugene, Oreg., USA) in 0.1 M PBS buffer, pH 8.0 for visualisation of the patterns. For cell seeding experiments, BSA-TR was omitted to avoid any unwanted non-specific interactions between BSA-TR and cells. After 10 min. of incubation with "ink" at room temperature, the stamps were rinsed in water for 20 s and dried for 1 min. under a N2 stream.

The activated RHCIII-MPC samples were placed in a Petri dish and then the upper surfaces were dried carefully with the N2 gas in preparation for µCP. The bottom corners of the hydrogel samples were left in contact with water to prevent complete dehydration and therefore undesired deformation of the hydrogels. Surfaces then were printed by applying the PDMS stamp onto the hydrogel surface. All printing was performed manually without any load, using the nitrogen stream to get the stamp into contact with the hydrogel surface. The stamp was left on for five minutes and then removed using tweezers. The patterned hydrogel surface was incubated with a solution containing 10 mM (PEG)3NH2 (Molecular Biosciences, Boulder, Colo., USA), in PBS, pH 8.0 for 40 min. to de-activate all remaining unreacted carboxyl groups. The surfaces were then carefully washed several times with fresh PBS, pH 7.3 and stored in this buffer solution prior to further use.

Characterization of Printed Hydrogels

To characterise the reproducibility of the µCP patterns, the optically transparent patterned hydrogels were imaged using an Olympus BX51 upright microscope (Olympus, Tokyo, Japan) equipped with a 10×, NA 0.3 water immersion objective and a Peltier-cooled Fview II CCD camera (Olympus Soft Imaging Solutions GmbH, Munster, Germany). Fluorescence images of fibronectin-BSA-TR® patterns were acquired and analysed using analySIS software (Olympus Soft Imaging Solutions GmbH, Münster, Germany).

The presence of FN in the micropatterns was confirmed by using a primary rabbit polyclonal antibody against FN (Abcam, Cambridge, UK), followed by a secondary antibody, donkey antirabbit IgG, conjugated with quantum dots Qdot655 (H+L) (Life Technologies, USA). To investigate the effect of µCP on the micro- and nanotopography of fully hydrated RHCIII-MPC constructs, atomic force microscopy (AFM) measurements were carried out with the samples fully immersed in 0.1 M PBS buffer, pH 7.3 using a NanoWizard® 3 AFM microscope (JPK Instruments AG, Berlin, Germany) mounted onto an Olympus IX81 (Olympus, Tokyo, Japan) inverted optical microscope to allow for combined optical and AFM imaging of the same surface. Sample topography images were obtained in contact mode using SNL-10 (Bruker, Billerica, Mass., USA) probes. Regions of interest for AFM analysis were selected with fluorescence microscopy to include the printed and unprinted zones of the surface within one large area (70×70 µm2) scan. Several different size scans were made. Images obtained were processed and the surface roughness was calculated using the region analysis tool within the AFM JPK data processing software.

Cytotoxicity Evaluation

All samples with 30 µm and 200 µm patterned stripes, and control samples comprising deactivated and unmodified hydrogels, were placed into 24-well plates. Immortalized human corneal epithelial cells (HCECs) from a cell line [27] were seeded onto the surface of the materials at a density of 2×104 cells per well. The HCECs were maintained in Keratinocyte Serum-Free Medium (KSFM; Life Technologies, Invitrogen, Paisley, UK) containing 50 µg/ml bovine pituitary extract and 5 ng/ml epidermal growth factor for 48 hours in a humidified 37° C. incubator. Cell viability was measured by using a Live/Dead staining kit (Life Technologies, Invitrogen, Paisley, UK), where cells were double-stained by calceinacetoxymethyl (Calcein AM) and ethidium homodimer-1 (EthD-1). The live cells displayed green fluorescence while the dead cells fluoresced red.

Cell Attachment and Proliferation

Green fluorescence protein (GFP) transfected HCECs were employed to facilitate cell counts. A stable GFP-HCEC cell line was established by transfection of HCEC with a vector containing a puromycin resistant gene together with GFP, using the Lipofectamine® 2000 Transfection Reagent (Life Technologies, California, USA). Selection of puromycin resistant cells with 2 µg/ml of puromycin added to the medium was performed to obtain stable GFP-lines. To examine proliferation rates on the different surfaces, 6 mm hydrogel discs with 30 µm and 200 µm FN striped patterns, and PEG-NH2 deactivated and unmodified samples, were placed within 96 well plates to fit snugly. Five thousand GFP-HCECs were seeded into each well. GFPHCECs were also seeded onto the tissue culture plate as a control for overall cell health. The cells were maintained in KSFM within a humidified 37° C. incubator with 5% CO2. Photomicrographs of the cells were taken at 2, 6, 24, 48 and 96 hours, using a fluorescence microscope (AxioVert A1, Carl Zeiss, Göttingen, Germany). Counts were made by sampling three different 1290×965 µm2 areas on each hydrogel surface.

Immunohistochemistry

GFP-HCECs were cultured on hydrogels for 4 days until when the cells reached confluence/near confluence on the patterns. Each sample was washed in 10 mM PBS, pH 7.4 and then fixed in 4% paraformaldehyde in PBS for 20 min. For permeabilization and blocking of unspecific binding, samples were incubated in PBS containing 0.25% Triton X-100 for 10 min. and 5% foetal calf serum (FCS) in PBST (0.05% Tween-20 in PBS) (FCS/PBST) for 1 hour, respectively. Samples were then incubated overnight at 4° C. with the following primary antibodies diluted in FCS/PBST:anti-proliferating cell protein Ki67 antibody (1:600) (Sigma-Aldrich, MO, USA), anti-focal adhesion kinase (FAK) antibody (1:500) (Abcam, Cambridge, UK) and antiintegrin beta 1 (integrin β1) antibody (1:200) (Abcam). After rinsing, the samples were exposed to the secondary antibody, Alexa Fluor-594 (1:400) (Invitrogen, Oregon, USA) at room temperature for 1 hour in the dark for visualisation. After another rinse, the samples were incubated with 4',6-diamidino-2-phenylindole dihydrochloride (DAPI) (PromoKine, Heidelberg, Germany) for 1 min. as nuclear counterstain. All samples were given a final rinse prior to mounting and examination under a confocal microscope (LSM700, Carl Zeiss, Göttingen, Germany). A total area of 50000 µm2 per sample was used for all the counts.

Results

RHCIII-MPC Hydrogels

A range of adjustments in hydrogel formulations were tested for producing a mechanically reinforced material suitable for post-fabrication of the implants. These included a starting RHCIII content of 13.7%, 18% and 20%; different RHC:MPC ratios and EDC:RHCIII-NH2 ratios. The resulting optical and mechanical properties of the hydrogels are given in Appendix A. The resulting enhancement in properties of RHCIII-MPC hydrogels after optimization of the above parameters as compared to previously published formulation. In both 13.7% and 18% RHCIII-MPC hydrogels, we found that a 2:1, RHCIII:MPC ratio with 0.4 EDC:RHCIII-NH2 gave the optimal formulations.

Increasing of the collagen content from 13.7% to 18% decreased the water content from 90.1±2.4% to approximately 86% (85.5±0.2% for RHCIII-MPC and 86.0±0.2% for RHCIII only). Hence, it turned out that the MPC content did not make much of a difference. Additionally, the EDC:RHCIII-NH2 ratio showed no obvious influence on the RI, while the RI increased with increasing MPC content within the gels.

The measured transmittance of white light decreased with the increased RHCIII concentration. Compared to the native cornea (transmittance: ~87%, backscatter: ~3%), however, all the RHCIII-MPC gels showed a higher transmittance and lower backscatter. The RHCIII only gels, on the other hand, exhibited a transmittance comparable to the native cornea (approx. 87%). All the cornea substitutes displayed a slightly lower RI of 1.35, which is that of water, compared to native cornea (1.37~1.38 [28]). In general, increasing the solids content of the hydrogels from 13.7% to 18% increased the tensile strength of RHCIII-MPC hydrogels from 1.29±0.31 MPa to 2.12±0.18 MPa. The tensile strengths of the 18% RHCIII only hydrogels were comparable to the 18% RHCIII-MPC hydrogels at 2.37±0.4 MPa. However, RHCIII only hydrogels were stiffer (an elastic modulus of 15.33±2.67 MPa) and less elastic (elongation at break of 28.21±2.01%) than corresponding RHCIII-MPC hydrogels (lower elastic modulus of 9.46±3.58 MPa; higher elongation at break of 33.34±3.87%). The 18% RHCIII-MPC hydrogels were more thermodynamically stable (Td=57.6° C.) than both the 18% RHCIII only (Td=53.1° C.) or 13.7% RHCIII-MPC hydrogels (Td=54.1° C.).

However, none were as stable as the native corneas (Td=65.1° C.). SEM imaging of cross-section of samples was performed for structural comparison of the produced RHCIII-MPC and RHCIII only hydrogels with native human corneas. A distinct lamellar structure could be seen for both human and biosynthetic corneas. The lamellar structure was observed throughout the entire cross-section of all samples while it was more homogeneous for the human cornea and better representative of the whole structure than that of the biosynthetic ones. In addition, the RHCIII-MPC hydrogels comprised lamellae-like layers interconnected by some tiny fiber-like structures, that better mimics the structure of the human cornea than the RHCIII crosslinked by EDC/NHS which had large lamellae without any interlamellar connections. However, the inner morphology of the biosynthetic corneas differed from their native counterpart in the number of lamella layers and the spacing between layers. For example, the lamella-like layers in the biosynthetic corneas were thicker and their number was lower compared to lamellas of the native cornea. In addition, the spacing between the ordered lattice structures of the native cornea was smaller (~15 microns) than that of the biosynthetic corneas (~150 microns). The lamella spacing for the human cornea had a wide size distribution ranging from 2 to 40 microns. Overall, despite some similarities between the biosynthetic corneas and their natural counterparts, the human cornea has a much more complex microstructure with higher degree of interconnectivity, as expected.

Precision Laser Profiling and Tissue Welding

The optimized hydrogels were sufficiently robust to allow complete cutting of "top-hat" implants using the femtosecond laser. The resulting mean dimensions of the cuts were: anterior diameter of the 5.9 mm, posterior diameter of 8.1 mm, and depth of 260 µm for the lamellar cut. For example, RHCIII-MPC hydrogels containing 18% RHCIII, with RHCIII:MPC=2:1 and EDC:RHCIII-NH2 (mol:mol)=0.4:1 (designated RHCIII-18/MPC(2/1)-E0.4), which had shown good mechanical properties, cut well with the laser. Top-hat shaped gels with precisely cut edges could be obtained. However, hydrogels with the lower 13.7% RHCIII content (but otherwise with same proportions of MPC and EDC crosslinker), fell apart during cutting.

Laser cut implants were successfully fitted into matched laser cut surgical beds. After riboflavin/UV-crosslinking, the implants remained permanently adhered to the corneal bed and sub-microscopical physical fibre-like connections were present between the implant and adjacent cornea when viewed by SEM. In contrast, implants detached completely in controls without UV radiation.

Overall Quality of the Microcontact Printed Patterns

The most stable RHCIII-18/MPC(2/1)-E0.4 hydrogels which lent themselves well to laser profiling were also optimal for μCP. The results show typical resulting striped FN patterns as visualized by staining with an anti-fibronectin antibody. Analysis of the fluorescence micrographs of the hydrogel samples confirmed good replication of the original patterns of the 30 and 200 μm stripes defined in the photo-lithographic mask production step. On the PDMS stamp, the width of the narrow stripes was 26.8±0.5 μm (based on brightfield microscopy), while that of the printed FN stripes was 27.1±0.8 μm. The thick stripes on the PDMS stamps and the resulting FN patterns had widths of 190.6±1.7 and 191.7±2.6 μm, respectively. The good reproducibility indicated that uncontrolled FN ink diffusion on partially dried collagen hydrogel samples was minimal. On the samples printed with 30 μm stripe pattern, the printed area occupied approx. 37% of the sample area, and approx. 32% of the total hydrogel surface was patterned and defect-free. On the 200 μm striped samples, the printed sample area occupied 40% of the sample and approximately 26% of the total hydrogel surface was printed and free from printing defects. Also, FN ink distribution on the entire patterned surface was satisfactorily homogeneous.

Atomic Force Microscopy

The effect of μCP on the micro- and nanotopography of fully hydrated RHCIII-MPC hydrogels was determined by AFM analysis. The original, unmodified collagen hydrogel surfaces appeared uneven, with irregularly arranged surface fibrils visible. The root mean square (RMS) of surface roughness as measured within a representative 2×2 μm2 scan area was 3.5 nm.

The regions of interest (ROIs) for AFM scans on the chemically activated and microcontact printed samples were identified by simultaneous fluorescence microscopy imaging. The AFM tip was positioned in the ROIs that were patterned with FN and BSA-TR® mixture. In topography images of the hydrogel surface after μCP and/or deactivation, the collagen fibrils appeared to be partially aligned, in contrast to the unmodified surface. However, the fine details of the collagen fibrils could not be resolved. There was no distinct overall height difference between the majority of the printed and adjacent unprinted area, either due to the high initial surface roughness and/or due to the ability to print a very thin, possibly monolayer thickness of FN. The edges of the stripes, however, were slightly corrugated by the printing and served to delineate the stripe boundaries. The RMS surface roughness of the FN-printed and unprinted regions on this particular sample, was very similar, at 1.3 nm and 1.4 nm, respectively. The AFM analysis therefore showed that the μCP resulted only in a very small change in the surface topology.

Effect of Patterning on Cytotoxicity, Cell Adhesion and Proliferation

Printing with PDMS stamps can result in a slight contamination of the sample surface with loose PDMS particles, but these can be removed by subsequent sample deactivation and washing steps. Live/dead staining performed indeed showed that there were no cytotoxic effects from the patterning. The numbers of dead cells (stained red) were negligible: 0 in most of the samples, 1-2 cells in a few others.

Analysis of the proliferation of HCECs on the different surfaces over time showed obvious differences between the patterned and non-patterned samples. The only two types where the growth rate could not be told apart (P>0.05) were the unmodified and deactivated RHCIII-MPC surfaces. The total number of cells counted per a defined ROI was highest on the hydrogels patterned with 200 μm stripes. However, when taking into account that the total FN-coated surface area per ROI was two times less on the 30 μm pattern than on the 200 μm pattern, the results show that the thinner stripes yielded approx. 26% more cells after normalization of the surface areas.

Immunohistochemistry and Cell Behaviour

The results show the behaviour of cells on the different surfaces. The integrin β1 family, which is involved binding ECM macromolecules including collagen and fibronectin, was expressed by HCECs growing on all groups. The proportion of integrin β1-expressing cells in the deactivated surfaces, 30 and 200 μm patterns, respectively, were significantly different from those growing on the unmodified RHCIII-MPC hydrogel surfaces, with the highest expression on the 30 μm stripes, although not that significantly different from the 200 μm stripes and deactivated surfaces (P>0.05). Immunohistochemical localization of FAK-positive cells showed that significantly more cells were growing on the 30 μm striped patterns that were positively stained (P≤0.05) than those of the other groups. Staining for the Ki67 protein associated with cell proliferation showed that the samples with 30 μm striped patterns supported a significantly larger proportion (P≤0.05) of positively stained cells than the other groups.

The invention claimed is:

1. A corneal implant having a first surface and a second surface, the corneal implant comprising:
    a matrix part containing a matrix material including a hydrogel of at least one first polymer and at least one second polymer, the first polymer including collagen or collagen mimetic peptide (CMP) provided with methacrylate or acrylate functional groups, the second polymer including a synthetic or a natural polymer having functional groups selected from thiol, acrylate or methacrylate, and the first and second polymers are crosslinked via said functional groups; and
    a core part in a central part of the matrix material, the core part including a core material of an interpenetrating network (IPN), the IPN including polymerized olefinic monomers, UV polymerizable monomers or a mixture thereof and the hydrogel of the matrix material, the core material exposed at the first surface and at the second surface, the core part being transparent such that the core part has a light transmission of at least 80% within a wavelength range of 400 nm to 700 nm, the core part being anti-fouling, the core part configured to block or hinder cell migration and vessel ingrowth.

2. The implant according to claim 1, wherein the core material includes 2-methacryloyloxyethyl phosphorylcholine-co-polyethylene glycol-diacrylate (MPC-co-PEGDA).

3. The implant according to claim 1, wherein the polymerized olefinic or UV polymerizable monomers are selected from poly methyl methacrylate (PMMA), poly-hydroxyethyl methacrylate (pHEMA), or pHEMA-poly ethylene glycol methacrylate (pHEMA-PEGMA).

4. The implant according to claim 1, wherein a surface of the matrix material or the core material is modified or patterned with PEGMA.

5. The implant according to claim 1, wherein a surface of the matrix material or the core material is modified or patterned with N-hydroxysulfosuccinimide (NHS), YIGSR polypeptides, IKVAV polypeptides, RGD polypeptides, ECM proteins, fibrinectine derived peptides, combinations of synergestic peptides, DGEA peptide from collagen, antibodies, glycosaminoglucans, motifs from growth factors, or pharmaceutically active substances.

6. The implant according to claim 2, wherein the MPC-co-PEGDA has at least 3 arms.

7. The implant according to claim 1, wherein the weight ratio of core material is 1 wt % or more of the total weight of the implant.

8. The implant according to claim 1, wherein the matrix material is cross-linked with a di-epoxide.

9. The implant according to claim 1, wherein
the first polymer is CMP,
the implant further includes a template polymer connected to the CMP, the template polymer having at least two arms, and
the matrix material includes CMP connected to the template polymer having at least two arms.

10. The implant according to claim 9, wherein the template polymer is a polyethylene glycol (PEG) template having 2, 4 or 6 arms.

11. The implant according to claim 10, wherein
the matrix material includes the CMP on the PEG template, and
the core material includes MPC-co-PEGDA.

12. The implant according to claim 9, wherein the methacrylate or acrylate groups are arranged along a triple helical chain of the CMP.

13. The implant according to claim 1, wherein the matrix material includes cellulose, carboxymethyl cellulose or silk.

14. The implant according to claim 1, wherein
the collagen or CMP are present in the form of fibrils, and
the fibrils are uniaxial orientated.

15. The implant according to claim 1, wherein
the first polymer is CMP, and
the implant further includes a template polymer connected to the CMP, the template polymer being a dendrimer.

16. A method of making the product according to claim 1, the method comprising:
providing a first aqueous solution of a first polymer of collagen or collagen mimetic peptide (CMP) including methacrylate or acrylate functional groups, wherein a template polymer is connected to the first polymer when the first polymer is CMP, the template polymer having at least two arms;
providing a second aqueous solution of a second polymer including a synthetic polymer having functional groups selected from thiol, acrylate or methacrylate, or synthetic monomers having thiol, acrylate or methacrylate functional groups;
forming the matrix material by cross-linking the first and second polymers;
adding core olefinic monomers, UV polymerizable monomers, polypeptides or a mixture thereof, and an initiator to a surface or a bulk of the matrix material; and
polymerizing the core olefinic monomers.

17. The method according to claim 16, wherein the adding includes diffusing an olefinic based material of the core olefinic monomers in the matrix material in at least 15 minutes.

18. The method according to claim 16, further comprising:
curing the product by UV radiation using a mask.

* * * * *